United States Patent
Sanders et al.

(10) Patent No.: US 11,473,144 B2
(45) Date of Patent: *Oct. 18, 2022

(54) METHODS FOR DETECTING CYSTIC FIBROSIS MUTATIONS USING MITRA TIP EXTRACTION

(71) Applicant: Quest Diagnostics Investments LLC, Secaucus, NJ (US)

(72) Inventors: Heather Sanders, San Juan Capistrano, CA (US); Nigel J. Clarke, Vista, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/461,356

(22) PCT Filed: Nov. 13, 2017

(86) PCT No.: PCT/US2017/061311
§ 371 (c)(1),
(2) Date: May 15, 2019

(87) PCT Pub. No.: WO2018/093723
PCT Pub. Date: May 24, 2018

(65) Prior Publication Data
US 2020/0056240 A1 Feb. 20, 2020

Related U.S. Application Data

(60) Provisional application No. 62/422,338, filed on Nov. 15, 2016.

(51) Int. Cl.
*C12Q 1/6883* (2018.01)
*C12Q 1/6806* (2018.01)
(Continued)

(52) U.S. Cl.
CPC ........ *C12Q 1/6883* (2013.01); *C12Q 1/6806* (2013.01); *C12Q 1/6827* (2013.01);
(Continued)

(58) Field of Classification Search
CPC .. C12Q 1/6883; C12Q 1/6806; C12Q 1/6827; C12Q 2600/112; C12Q 2600/156; C12Q 2600/158; C12Q 2600/16
See application file for complete search history.

(56) References Cited

U.S. PATENT DOCUMENTS

| | | |
|---|---|---|
| 4,843,155 A | 6/1989 | Chomczynski |
| 5,840,702 A | 11/1998 | Bedwell |

(Continued)

FOREIGN PATENT DOCUMENTS

| | | |
|---|---|---|
| JP | 2008-546404 A | 12/2008 |
| JP | 2013-528058 A | 7/2013 |

(Continued)

OTHER PUBLICATIONS

MacIntyre et al. (The Lancet, 1991, 338:869-871) (Year: 1991).*

(Continued)

*Primary Examiner* — Jeremy C Flinders
(74) *Attorney, Agent, or Firm* — Foley & Lardner LLP

(57) ABSTRACT

The present disclosure provides methods for determining whether a patient exhibiting cystic fibrosis symptoms, or a patient at risk for cystic fibrosis, will benefit from treatment with one or more anti-cystic fibrosis therapeutic agents. These methods are based on detecting hereditary cystic fibrosis related mutations in small-volume dried biological fluid samples that are collected using a volumetric absorptive microsampling device. Kits for use in practicing the methods are also provided.

15 Claims, 2 Drawing Sheets

(51) Int. Cl.
*C12Q 1/6827* (2018.01)
*A61P 43/00* (2006.01)

(52) U.S. Cl.
CPC .. *C12Q 2600/112* (2013.01); *C12Q 2600/156* (2013.01); *C12Q 2600/158* (2013.01); *C12Q 2600/16* (2013.01)

(56) References Cited

U.S. PATENT DOCUMENTS

| | | | |
|---|---|---|---|
| 9,102,924 | B2 | 8/2015 | Bauer et al. |
| 2003/0049608 | A1 | 3/2003 | Bahl et al. |
| 2004/0009924 | A1 | 1/2004 | Stoven et al. |
| 2011/0082050 | A1 | 4/2011 | Hantash |
| 2012/0003643 | A1 | 1/2012 | Christensen et al. |
| 2013/0116597 | A1* | 5/2013 | Rudge .............. A61B 5/150305 600/575 |
| 2013/0237432 | A1 | 9/2013 | Li et al. |
| 2016/0068906 | A1 | 3/2016 | Sjogren et al. |
| 2016/0281166 | A1 | 9/2016 | Bhattacharjee et al. |

FOREIGN PATENT DOCUMENTS

| | | |
|---|---|---|
| JP | 2013-529472 A | 7/2013 |
| WO | WO-2006/137733 A1 | 12/2006 |
| WO | WO-2011/155833 A2 | 12/2011 |
| WO | WO-2013/067520 A1 | 5/2013 |

OTHER PUBLICATIONS

Qiagen® (Genomic DNA Handbook, Jun. 2015) (Year: 2015).*
Wong et al. (Current Protocols in Molecular Biology 7.11.1-7.11.11) (Year: 2013).*
Chomczynski et al,. "The single-step method of RNA isolation by acid guanidinium thiocyanate-phenol-chloroform extraction: twenty-something years on," Nature Protocols, Feb. 2006, 1(2):581-585.
International Search Report and Written Opinion dated Mar. 20, 2018 as issued in corresponding International Application No. PCT/US2017/061311.
International Search Report dated May 4, 2018, as issued in International Application No. PCT/US2017/061303.
Lakshmi et al., "Application of Real Time Loop Mediated Isothermal Amplification Assay on Dried Blood Spots in the Detection of HCV RNA among High Risk Patients," Journal of Emerging Diseases and Virology, 2(1): doi http://dx.doi.org/10.16966/jved.111.
Spooner et al., "A device for dried blood microsampling in quantitative bioanalysis: overcoming the issues associated with blood hematocrit," Bioanalysis, 2015, 7(6):653-659.
Denniff et al., "Volumetric Absorptive Microsampling: A Dried Sample Collection Technique for Quantitative Bioanalysis," Analytical Chemistry, Aug. 19, 2014, 86(16):8489-8495.
Enderle et al., "Clinical feasibility of dried blood spots: Analytics, validation, and applications," Journal of Pharmaceutical and Biochemical Analysis, Jun. 23, 2016, 130:231-243.
Spooner et al., "A device for dried blood microsampling in quantitative bioanalysis: overcoming the issues associated with blood hematocrit," Bioanalysis, Apr. 1, 2015, 7(6):653-659.
Supplementary European Search Report dated Apr. 1, 2020 in EP 17872827.5.
Madej et al,. "International Standards and Reference Materials for Quantitative Molecular Infectious Disease Testing," Journal of Molecular Diagnostics, Mar. 2010, 12(2):133-143.
Martell et al., "High-Throughput Real-Time Reverse Transcription-PCR Quantitation of Hepatitis C Virus RNA," Journal of Clinical Microbiology, Feb. 1999, 37(2):327-332.
Non-Final Office Action dated Sep. 4, 2020, in U.S. Appl. No. 15/811,463.
Poiteau et al., "Performance of rapid diagnostic tests for the detection of antibodies to hepatitis C virus in whole blood collected on dried blood spots," Journal of Viral Hepatitis, May 1, 2016, 23(5):399-401.
Supplementary European Search Report in EP 17871443.2 dated May 13, 2020.
Non-Final Office Action dated Jun. 18, 2020 in U.S. Appl. No. 15/811,550.
Non-Final Office Action in U.S. Appl. No. 16/349,976 dated Nov. 24, 2020.
Soulier et al,. "Dried Blood Spots: A Tool to Ensure Broad Access to Hepatitis C Screening, Diagnosis, and Treatment Monitoring," The Journal of Infectious Diseases, 2016 (online Sep. 2, 2015), 213:1087-1095.
Anslinger et al., "Application of the BioRobot EZ1 in a forensic laboratory," Legal medicine, 2005, 7:164-168.
Esfahani et al., "Rapid and simple detection of Hepatitis C virus by reverse transcriptase-loop-mediated isothermal amplification method," African Journal of Microbiology Research, Dec. 4, 2010, 4(23):2580-2586.
Kargar et al., "Loop-Mediated Isothermal Amplification Assay for Rapid Detection of Hepatitis C virus," Indian J. Virol., Jan.-Jun. 2012, 23(1):18-23.
Office Action dated Aug. 31, 2021 in JP 2019-546775, with English translation.
Office Action dated Sep. 21, 2021, in JP 2019-546776, with English translation.
Parker et al., "A method for the detection and confirmation of antibodies to hepatitis C virus in dried blood spots," Journal of Virological Methods, 1997, 68:199-205.
Yang et al., "Detection of hepatitis C virus by an improved loop-mediated isothermal amplification assay," Arch. Virol., 2011, 156:1387-1396.
Office Action dated Feb. 8, 2022 in JP 2019-546776, with English translation.

* cited by examiner

METHODS FOR DETECTING CYSTIC FIBROSIS MUTATIONS USING MITRA TIP EXTRACTION

TECHNICAL FIELD

The present disclosure provides methods for determining whether a patient exhibiting cystic fibrosis symptoms, or a patient at risk for cystic fibrosis, will benefit from treatment with one or more anti-cystic fibrosis therapeutic agents. These methods are based on detecting hereditary cystic fibrosis related mutations in small-volume dried biological fluid samples that are collected using a volumetric absorptive microsampling device. Alterations in target nucleic acid sequences corresponding to one or more cystic fibrosis related mutations may be detected using next generation sequencing (NGS). Kits for use in practicing the methods are also provided.

BACKGROUND

The following description of the background of the present disclosure is provided simply to aid the reader in understanding the disclosure and is not admitted to describe or constitute prior art to the present disclosure.

Cystic fibrosis (CF) is the most common severe autosomal recessive genetic disorder in the Caucasian population. It affects approximately 1 in 2,500 live births in North America (Boat et al., *The Metabolic Basis of Inherited Disease*, 6th ed., pp 2649-2680, McGraw Hill, NY (1989)). Approximately 1 in 25 persons of northern European Caucasian descent are carriers of the disease. The responsible gene has been localized to a 250,000 base pair genomic sequence present on the long arm of chromosome 7. This sequence encodes a membrane-associated protein called the "cystic fibrosis transmembrane regulator" (or "CFTR"). There are greater than 1000 different mutations in the CFTR gene, each having varying frequencies of occurrence in different populations, presently reported to the Cystic Fibrosis Genetic Analysis Consortium. These mutations exist in both the coding regions (e.g., ΔF508, a mutation found in about 70% of CF alleles, represents a deletion of a phenylalanine residue at position 508) and the non-coding regions (e.g., the 5T, 7T, and 9T variants correspond to a sequence of 5, 7, or 9 thymidine bases located at the splice branch/acceptor site of intron 8) of the CFTR gene.

The major symptoms of cystic fibrosis include chronic pulmonary disease, pancreatic exocrine insufficiency, and elevated sweat electrolyte levels. The symptoms are consistent with cystic fibrosis being an exocrine disorder. Although recent advances have been made in the analysis of ion transport across the apical membrane of the epithelium of CF patient cells, it is not clear that the abnormal regulation of chloride channels represents the primary defect in the disease.

Next-generation sequencing (NGS) is extensively used in diagnostics of genetic disorders, including cystic fibrosis, due to its high data throughput and ability to detect multiple gene alterations in a single assay. However, the procedures associated with collecting and preparing nucleic acids from biological samples (e.g., blood) are usually cumbersome, and often require specialized equipment or technical skill. Further, certain patient groups, such as the elderly or infants, are unable to provide large volumes of blood for recurrent testing.

Thus, there is a need for rapid and non-invasive methods for determining whether a patient has a genetic basis for developing cystic fibrosis or is at risk of producing offspring that will suffer from cystic fibrosis.

SUMMARY

In one aspect, the present disclosure provides a method for detecting at least one mutation in a sample CFTR nucleic acid comprising (a) extracting the sample CFTR nucleic acid from a dried biological fluid sample eluted from an absorbent tip of a microsampling device; (b) generating a library comprising amplicons corresponding to a plurality of target segments of the sample CFTR nucleic acid; and (c) detecting at least one mutation in at least one of the amplicons in the library using high throughput massive parallel sequencing.

Additionally or alternatively, in some embodiments, the dried biological fluid sample is dried plasma, dried serum, or dried whole blood. In some embodiments, the dried biological fluid sample on the absorbent tip of the microsampling device is collected from a patient via fingerstick. In some embodiments, the microsampling device is a volumetric absorbent microsampling device. In certain embodiments, the microsampling device is a MITRA® tip.

Additionally or alternatively, in some embodiments, elution of the dried biological fluid sample is performed by contacting the absorbent tip of the microsampling device with a lysis buffer and Proteinase K. In certain embodiments, the lysis buffer comprises guanidine hydrochloride, Tris.Cl, EDTA, Tween 20, and Triton X-100. In a further embodiment, the lysis buffer comprises 800 mM guanidine hydrochloride; 30 mM Tris.Cl, pH 8.0; 30 mM EDTA, pH 8.0; 5% Tween 20; and 0.5% Triton X-100. In other embodiments, the lysis buffer comprises 2.5-10% sodium dodecyl sulphate.

Additionally or alternatively, in some embodiments, elution of the dried biological fluid sample is performed by contacting the absorbent tip of the microsampling device with the lysis buffer for up to 15 minutes at 90° C. In certain embodiments, elution of the dried biological fluid sample is performed by contacting the absorbent tip of the microsampling device with Proteinase K for up to 1 hour at 56° C. In other embodiments, elution of the dried biological fluid sample is performed by contacting the absorbent tip of the microsampling device with Proteinase K for up to 16-18 hours at 56° C.

In some embodiments, the sample volume of the microsampling device is no more than 10-20 μL. In some embodiments, no more than 400 ng of genomic DNA is eluted from the absorbent tip of the microsampling device. In other embodiments, about 100 ng to about 400 ng of genomic DNA is eluted from the absorbent tip of the microsampling device. In some embodiments, the method further comprises ligating an adapter sequence to the ends of the plurality of amplicons. The adapter sequence may be a P5 adapter, P7 adapter, P1 adapter, A adapter, or Ion Xpress™ barcode adapter. Additionally or alternatively, in some embodiments, the method further comprises hybridizing one or more bait sequences to one or more target segments of the sample CFTR nucleic acid.

Additionally or alternatively, in some embodiments, the at least one mutation is selected from among a base change, a gene deletion and a gene duplication. Additionally or alternatively, in some embodiments, the at least one mutation is associated with cystic fibrosis, and may include one or more mutations listed in Table 2.

In any of the above embodiments, the dried biological fluid sample is obtained from an individual exhibiting cystic fibrosis symptoms, or having a family history of cystic fibrosis or a CFTR mutation. In some embodiments, the dried biological fluid sample is obtained from a male partner of an obstetrics and gynecology patient having cystic fibrosis or at least one CFTR mutation.

Additionally or alternatively, in some embodiments, the plurality of target segments, taken together, span all coding and non-coding regions of the CFTR gene. In some embodiments, the plurality of target segments further span about 1000 nucleotides of a promoter region immediately upstream of the first exon of the CFTR gene. In some embodiments, the plurality of target segments further span about 200 to 350 nucleotides immediately downstream of the CFTR gene.

Additionally or alternatively, in some embodiments, the high throughput massive parallel sequencing is performed using pyrosequencing, reversible dye-terminator sequencing, SOLiD sequencing, Ion semiconductor sequencing, Helioscope single molecule sequencing, sequencing by synthesis, sequencing by ligation, or SMRT™ sequencing. In certain embodiments, the high throughput massive parallel sequencing involves a read depth approach. Additionally or alternatively, in some embodiments, the plurality of amplicons further comprise a unique index sequence.

In another aspect, the present disclosure provides a method for detecting at least one mutation in a sample CFTR nucleic acid comprising generating a library comprising amplicons corresponding to a plurality of target segments of the sample CFTR nucleic acid, wherein the sample CFTR nucleic acid is extracted from a dried biological fluid sample eluted from an absorbent tip of a microsampling device with a lysis buffer and Proteinase K. In a further embodiment, the at least one mutation in the sample CFTR nucleic acid is detected using high throughput massive parallel sequencing. In some embodiments, the lysis buffer comprises guanidine hydrochloride, Tris.Cl, EDTA, Tween 20, and Triton X-100.

Additionally or alternatively, in some embodiments, the plurality of target segments of the sample CFTR nucleic acid comprise at least one alteration compared to the corresponding region of a reference CFTR nucleotide sequence. In certain embodiments, the reference CFTR nucleotide sequence comprises a wild-type CFTR nucleic acid sequence.

In one aspect, the present disclosure provides a method for selecting a patient exhibiting cystic fibrosis symptoms, or a patient at risk for cystic fibrosis for treatment with an anti-cystic fibrosis therapeutic agent comprising (a) eluting a dried biological fluid sample of the patient from an absorbent tip of a microsampling device, wherein the dried biological fluid sample comprises a sample CFTR nucleic acid; (b) generating a library comprising amplicons corresponding to a plurality of target segments of the sample CFTR nucleic acid; (c) detecting at least one mutation in at least one of the amplicons in the library using high throughput massive parallel sequencing; and (d) selecting the patient for treatment with an anti-cystic fibrosis therapeutic agent. The dried biological fluid sample may be dried plasma, dried serum, or dried whole blood. In some embodiments, the microsampling device is a volumetric absorbent microsampling device. In certain embodiments, the dried biological fluid sample on the absorbent tip of the microsampling device is collected from a patient via fingerstick. In certain embodiments, the microsampling device is a MITRA® tip. In some embodiments, the patient harbors one or more mutations in the CFTR gene and may include one or more mutations listed in Table 2.

In any of the above embodiments, the anti-cystic fibrosis therapeutic agent is one or more agents selected from the group consisting of penicillin, amoxicillin, cephalosporins, macrolides, fluoroquinolones, sulfonamides, Tetracyclines, aminoglycosides, colistin, Amcinonide, Betamethosone diproprionate, Clobetasol, Clocortolone, Dexamethasone, Diflorasone, Dutasteride, Flumethasone Pivalate, Flunisolide, Fluocinolone Acetonide, Fluocinonide, Fluorometholone, Fluticasone propionate, Fluticasone propionate, Fluticasone propionate, Flurandrenolide, Hydroflumethiazide, aceclofenac, acemetacin, aspirin, celecoxib, dexibuprofen, dexketoprofen, diclofenac, etodolac, etoricoxib, fenoprofen, flurbiprofen, ibuprofen, indometacin, ketoprofen, mefenamic acid, meloxicam, nabumetone, naproxen, sulindac, tenoxicam, tiaprofenic acid, expectorants, antihistamines, cough suppressants, Dextromethorphan, hypertonic salines, dornase alfa, mucolytics, pancreatic enzymes, vitamin A, vitamin D, vitamin E, vitamin K, and supplements reduce stomach acid.

In another aspect, the present disclosure provides a method for detecting a genetic basis for being affected with cystic fibrosis, or for being a cystic fibrosis carrier in an individual comprising: (a) generating an amplicon library by amplifying multiple target segments of a CFTR nucleic acid obtained from the individual, wherein the sample CFTR nucleic acid is extracted from a dried biological fluid sample eluted from an absorbent tip of a microsampling device; (b) sequencing the amplicons in the amplicon library using high throughput massive parallel sequencing, and (c) detecting a genetic basis for being affected with cystic fibrosis, or for being a cystic fibrosis carrier when the nucleotide sequence of one or more of the target segments of the CFTR nucleic acid comprises a mutation associated with cystic fibrosis.

Also provided herein are kits for detecting at least one mutation in a sample CFTR nucleic acid in a dried biological fluid sample comprising a skin puncture tool, a volumetric absorptive microsampling device, a lysis buffer, and proteinase K, wherein the at least one mutation comprises one or more of the CFTR mutations listed in Table 2.

Additionally or alternatively, in some embodiments, the kits further comprise one or more primer pairs that hybridize to one or more target segments of the sample CFTR nucleic acid. In some embodiments, the kits further comprise one or more bait sequences that hybridize to one or more target segments of the sample CFTR nucleic acid. In some embodiments, the lysis buffer comprises guanidine hydrochloride, Tris.Cl, EDTA, Tween 20, and Triton X-100.

In any of the above embodiments of the kits of the present technology, the volumetric absorptive microsampling device is a MITRA® tip.

BRIEF DESCRIPTION OF THE DRAWINGS

FIG. 1 demonstrates that dual-tip extraction on average results in a 2-fold increase in DNA yield.

FIG. 2 demonstrates that all 7 MITRA® tip specimens exceeded the minimum QC criteria for all covered CFTR target regions in a fully burdened 384 sample run (i.e., the specimens were run on a plate that was performed at full capacity, i.e., 377 operations samples (Ops) and 7 MITRA® tip samples).

DETAILED DESCRIPTION

Figure 1:
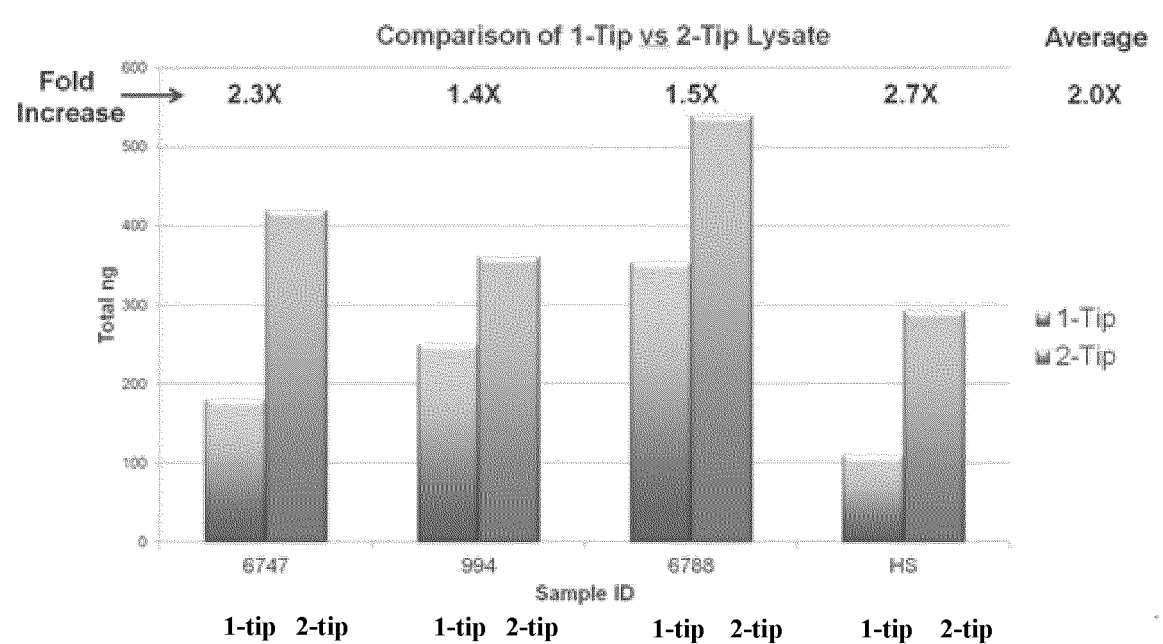
FIG. 1 shows a comparison of the DNA yield from one-tip versus dual-tip extraction from MITRA® tips using the DNA Investigator kit on the QIAsymphony® automated extraction platform. For dual-tip extraction, the lysates eluted from two individual MITRA® tips from the same patient were combined together.

The present disclosure provides methods for determining whether a patient exhibiting cystic fibrosis symptoms, or a patient at risk for cystic fibrosis, will benefit from treatment with one or more anti-cystic fibrosis therapeutic agents. These methods are based on detecting hereditary cystic fibrosis-related mutations in small-volume dried biological fluid samples that are collected using a volumetric absorptive microsampling device. Kits for use in practicing the methods are also provided.

Definitions

Unless otherwise defined, all technical and scientific terms used herein have the same meaning as commonly understood by one of ordinary skill in the art to which the present technology belongs.

As used herein, the term "about" in reference to a number is generally taken to include numbers that fall within a range of 1%-10% in either direction (greater than or less than) of the number unless otherwise stated or otherwise evident from the context.

The term "adapter" refers to a short, chemically synthesized, nucleic acid sequence which can be used to ligate to the end of a nucleic acid sequence in order to facilitate attachment to another molecule. The adapter can be single-stranded or double-stranded. An adapter can incorporate a short (typically less than 50 base pairs) sequence useful for PCR amplification or sequencing.

As used herein, the "administration" of a therapeutic agent or drug to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, an "alteration" of a gene or gene product (e.g., a marker gene or gene product) refers to the presence of a mutation or mutations within the gene or gene product, e.g., a mutation, which affects the quantity or activity of the gene or gene product, as compared to the normal or wild-type gene. The genetic alteration can result in changes in the quantity, structure, and/or activity of the gene or gene product in a diseased tissue or cell, as compared to its quantity, structure, and/or activity, in a normal or healthy tissue or cell (e.g., a control). For example, an alteration which is associated with cystic fibrosis may have an altered nucleotide sequence (e.g., a mutation), amino acid sequence, chromosomal translocation, intra-chromosomal inversion, copy number, expression level, protein level, protein activity, of the gene encoding the membrane-associated protein "cystic fibrosis transmembrane regulator" (or "CFTR") in a diseased tissue or cell, as compared to that observed within a normal, healthy tissue or cell. Exemplary mutations include, but are not limited to, point mutations (e.g., silent, missense, or nonsense), deletions, insertions, inversions, linking mutations, duplications, translocations, inter- and intra-chromosomal rearrangements. Mutations can be present in the coding or non-coding region of the gene. In certain embodiments, the alterations are associated with a phenotype, e.g., a phenotype associated with cystic fibrosis.

As used herein, the terms "amplify" or "amplification" with respect to nucleic acid sequences, refer to methods that increase the representation of a population of nucleic acid sequences in a sample. Copies of a particular target nucleic acid sequence generated in vitro in an amplification reaction are called "amplicons" or "amplification products". Amplification may be exponential or linear. A target nucleic acid may be DNA (such as, for example, genomic DNA and cDNA) or RNA. While the exemplary methods described hereinafter relate to amplification using polymerase chain reaction (PCR), numerous other methods such as isothermal methods, rolling circle methods, etc., are well known to the skilled artisan. The skilled artisan will understand that these other methods may be used either in place of, or together with, PCR methods. See, e.g., Saiki, "*Amplification of Genomic DNA*" in PCR Protocols, Innis et al., Eds., Academic Press, San Diego, Calif. 1990, pp 13-20; Wharam, et al., *Nucleic Acids Res.* 29(11):E54-E54 (2001).

"Bait", as used herein, is a type of hybrid capture reagent that retrieves target nucleic acid sequences for sequencing. A bait can be a nucleic acid molecule, e.g., a DNA or RNA molecule, which can hybridize to (e.g., be complementary to), and thereby allow capture of a target nucleic acid. In one embodiment, a bait is an RNA molecule (e.g., a naturally-occurring or modified RNA molecule); a DNA molecule (e.g., a naturally-occurring or modified DNA molecule), or a combination thereof. In other embodiments, a bait includes a binding entity, e.g., an affinity tag, that allows capture and separation, e.g., by binding to a binding entity, of a hybrid formed by a bait and a nucleic acid hybridized to the bait. In one embodiment, a bait is suitable for solution phase hybridization.

As used herein, "bait set" refers to one or a plurality of bait molecules.

The term "carrier state" or "cystic fibrosis carrier" as used herein means a person who harbors a CFTR allele that has a mutant CFTR nucleic acid sequence associated with cystic fibrosis, and a second allele that is not a mutant CFTR nucleic acid sequence. Cystic fibrosis is an "autosomal recessive" disease, meaning that a mutation produces little or no phenotypic effect when present in a heterozygous state with a non-disease related allele, but produces a "disease state" when a person is homozygous or a compound heterozygote, i.e., both CFTR alleles are mutant CFTR nucleic acid sequences.

A "CFTR nucleic acid" as used herein refers to a nucleic acid that contains a sequence of a CFTR gene, mRNA, cDNA or a portion of such a CFTR sequence. A CFTR nucleic acid may contain the CFTR coding region. A CFTR nucleic acid may be genomic DNA, cDNA, single stranded DNA or mRNA. In some embodiments, only a single strand of a sample CFTR nucleic acid is amplified and/or sequenced. In some embodiments both strands of double stranded CFTR DNA are amplified and sequenced. A CFTR nucleic acid may be present in a biological sample or it may be isolated from a biological sample.

The term "CFTR promoter region" as used herein refers to a segment of the CFTR gene representing at least the first 250 nucleotides (nt) upstream from the translation start site. In other embodiments, the promoter region may include the first 250 nt, first 300 nt, first 350 nt, first 400 nt, first 450 nt, first 500 nt, first 1 kb, first 5 kb, first 10, kb, first 15, kb, first 20, kb, first 21 kb, or first 22 kb of sequence directly upstream of the start codon. A deletion of the promoter region as defined herein may be accompanied by deletion of downstream exons/introns but not all of the CFTR gene. In some embodiments, the coordinate deletion involving the CFTR promoter region and downstream CFTR gene sequence involves about less than 10 exons, and more typically involves less than 5 exons. Deletions or duplications of the CFTR promoter region may be detected using primers that flank the deleted or duplicated sequence. In certain embodiments, a promoter deletion or duplication involves a segment of at least one or more nucleotides, at least four or more nucleotides, at least 5 or more nucleotides, at least 8 or more nucleotides, or at least 12 or more nucleotides.

The term "coding sequence" as used herein means a sequence of a nucleic acid or its complement, or a part thereof, that can be transcribed and/or translated to produce the corresponding mRNA, and/or polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced there from. The term "non-coding sequence" as used herein means a sequence of a nucleic acid or its complement, or a part thereof, that is not transcribed into amino acids in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

The terms "complement", "complementary" or "complementarity" as used herein with reference to polynucleotides (i.e., a sequence of nucleotides such as an oligonucleotide or a target nucleic acid) refer to the Watson/Crick base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-S'." Certain bases not commonly found in naturally-occurring nucleic acids may be included in the nucleic acids described herein. These include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be an RNA sequence complementary to the DNA sequence or its complement sequence, and can also be a cDNA.

The term "substantially complementary" as used herein means that two sequences hybridize under stringent hybridization conditions. The skilled artisan will understand that substantially complementary sequences need not hybridize along their entire length. In particular, substantially complementary sequences may comprise a contiguous sequence of bases that do not hybridize to a target sequence, positioned 3' or 5' to a contiguous sequence of bases that hybridize under stringent hybridization conditions to a target sequence.

As used herein, a "control" or "reference" is an alternative sample used in an experiment for comparison purpose. A control can be "positive" or "negative." A "control nucleic acid sample" or "reference nucleic acid sample" as used herein, refers to nucleic acid molecules from a control or reference sample. In certain embodiments, the reference or control nucleic acid sample is a wild-type or a non-mutated DNA or RNA sequence. In certain embodiments, the reference nucleic acid sample is purified or isolated (e.g., it is removed from its natural state). In other embodiments, the reference nucleic acid sample is from a non-diseased sample, e.g., a blood control, a tissue control, or any other non-diseased sample from the same or a different subject.

"Coverage depth" refers to the number of nucleotides from sequencing reads that are mapped to a given position.

The term "deletion" as used herein encompasses a mutation that removes one or more nucleotides from nucleic acid. Conversely, the term "duplication" refers to a mutation that inserts one or more nucleotides of identical sequence directly next to this sequence in the nucleic acid. In some embodiments, a deletion or duplication involves a segment of four or more nucleotides.

As used herein, the term "detecting" refers to determining the presence of a mutation or alteration in a nucleic acid of interest in a sample. Detection does not require the method to provide 100% sensitivity.

The term "dosage" or "gene dosage" refers to the number of copies of a gene, or portions of a gene, present in a sample.

As used herein, the term "effective amount" refers to a quantity sufficient to achieve a desired therapeutic and/or prophylactic effect, e.g., an amount which results in the prevention of onset of or the amelioration in one or more symptoms associated with cystic fibrosis. In the context of therapeutic or prophylactic applications, the amount of a therapeutic agent administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. As used herein, a "therapeutically effective amount" of a therapeutic drug or agent is meant levels in which the physiological effects of a hereditary disorder such as cystic fibrosis are, at a minimum, ameliorated. A therapeutically effective amount can be given in one or more administrations.

As used herein, the terms "extraction" or "isolation" refer to any action taken to separate nucleic acids from other cellular material present in the sample. The term extraction or isolation includes mechanical or chemical lysis, addition of detergent or protease, or precipitation and removal of other cellular material.

The term "flanking" as used herein with regard to primers means that a primer hybridizes to a target nucleic acid adjoining a region of interest sought to be amplified on the target. The skilled artisan will understand that optimal primers are pairs of primers that hybridize 5' from a region of interest, one on each strand of a target double stranded DNA molecule, such that nucleotides may be added to the 3' end of the primer by a suitable DNA polymerase. Primers that flank a CFTR exon are generally designed not to anneal to the exon sequence but rather to anneal to sequence that adjoins the exon (e.g., intron sequence). However, in some embodiments, amplification primer may be designed to anneal to the exon sequence.

"Gene" as used herein refers to a DNA sequence that comprises regulatory and coding sequences necessary for the production of an RNA, which may have a non-coding function (e.g., a ribosomal or transfer RNA) or which may include a polypeptide or a polypeptide precursor. The RNA or polypeptide may be encoded by a full length coding sequence or by any portion of the coding sequence so long as the desired activity or function is retained. Although a sequence of the nucleic acids may be shown in the form of DNA, a person of ordinary skill in the art recognizes that the corresponding RNA sequence will have a similar sequence with the thymine being replaced by uracil, i.e., "T" is replaced with "U."

A "genetic basis for cystic fibrosis" in an individual refers to the individual's genotype, in particular, of their CFTR nucleic acids and whether the individual possesses at least one CFTR mutation that contributes to cystic fibrosis. The term "wild-type" as used herein with respect to the CFTR gene or a locus thereof refers to the CFTR gene sequence which is found in NCBI GenBank locus IDs M58478 (HUMCFTC), AC000111 and AC000061. A cDNA for a CFTR gene may be found in Audrezet et al., *Hum. Mutat.* 23(4), 343-357 (2004) and/or Genbank accession number NM_000492.3. A "rare CFTR mutation" is a mutation in the CFTR gene sequence that is present in <0.1% of cystic fibrosis patients. A "private CFTR mutation" is a mutation in the CFTR gene sequence that is only found in a single family or a small group. A "common CFTR mutation" is a mutation in the CFTR gene sequence that is associated with cystic fibrosis and is present in at least 0.1% of patients with cystic fibrosis.

The term "hybridize" as used herein refers to a process where two substantially complementary nucleic acid strands (at least about 65% complementary over a stretch of at least 14 to 25 nucleotides, at least about 75%, or at least about 90% complementary) anneal to each other under appropriately stringent conditions to form a duplex or heteroduplex through formation of hydrogen bonds between complementary base pairs. Hybridizations are typically and preferably conducted with probe-length nucleic acid molecules, preferably 15-100 nucleotides in length, more preferably 18-50 nucleotides in length. Nucleic acid hybridization techniques are well known in the art. See, e.g., Sambrook, et al., 1989, *Molecular Cloning: A Laboratory Manual*, Second Edition, Cold Spring Harbor Press, Plainview, N.Y. Hybridization and the strength of hybridization (i.e., the strength of the association between the nucleic acids) is influenced by such factors as the degree of complementarity between the nucleic acids, stringency of the conditions involved, and the thermal melting point ($T_m$) of the formed hybrid. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, *Molecular Cloning: A Laboratory Manual*, Second Edition, Cold Spring Harbor Press, Plainview, N.Y.; Ausubel, F. M. et al. 1994, *Current Protocols in Molecular Biology*, John Wiley & Sons, Secaucus, N.J. In some embodiments, specific hybridization occurs under stringent hybridization conditions. An oligonucleotide or polynucleotide (e.g., a probe or a primer) that is specific for a target nucleic acid will "hybridize" to the target nucleic acid under suitable conditions.

As used herein, the terms "individual", "patient", or "subject" can be an individual organism, a vertebrate, a mammal, or a human. In a preferred embodiment, the individual, patient or subject is a human.

As used herein, the term "library" refers to a collection of nucleic acid sequences, e.g., a collection of nucleic acids derived from whole genomic, subgenomic fragments, cDNA, cDNA fragments, RNA, RNA fragments, or a combination thereof. In one embodiment, a portion or all of the library nucleic acid sequences comprises an adapter sequence. The adapter sequence can be located at one or both ends. The adapter sequence can be useful, e.g., for a sequencing method (e.g., an NGS method), for amplification, for reverse transcription, or for cloning into a vector.

The library can comprise a collection of nucleic acid sequences, e.g., a target nucleic acid sequence (e.g., a CFTR nucleic acid sequence), a reference nucleic acid sequence, or a combination thereof). In some embodiments, the nucleic acid sequences of the library can be derived from a single subject. In other embodiments, a library can comprise nucleic acid sequences from more than one subject (e.g., 2, 3, 4, 5, 6, 7, 8, 9, 10, 20, 30 or more subjects). In some embodiments, two or more libraries from different subjects can be combined to form a library having nucleic acid sequences from more than one subject. In one embodiment, the subject is a human having, or at risk of having, a cystic fibrosis.

A "library nucleic acid sequence" refers to a nucleic acid molecule, e.g., a DNA, RNA, or a combination thereof, that is a member of a library. Typically, a library nucleic acid sequence is a DNA molecule, e.g., genomic DNA or cDNA. In some embodiments, a library nucleic acid sequence is fragmented, e.g., sheared or enzymatically prepared, genomic DNA. In certain embodiments, the library nucleic acid sequences comprise sequence from a subject and sequence not derived from the subject, e.g., adapter sequence, a primer sequence, or other sequences that allow for identification, e.g., "barcode" sequences. In some embodiments, the library comprises amplicons corresponding multiple segments of a target nucleic acid sequence, such as a sample CFTR nucleic acid sequence.

The term "multiplex PCR" as used herein refers to amplification of two or more products which are each primed using a distinct primer pair.

"Next generation sequencing or NGS" as used herein, refers to any sequencing method that determines the nucleotide sequence of either individual nucleic acid molecules (e.g., in single molecule sequencing) or clonally expanded proxies for individual nucleic acid molecules in a high throughput parallel fashion (e.g., greater than $10^3$, $10^4$, $10^5$ or more molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. *Nature Biotechnology Reviews* 11:31-46 (2010).

As used herein, "oligonucleotide" refers to a molecule that has a sequence of nucleic acid bases on a backbone comprised mainly of identical monomer units at defined intervals. The bases are arranged on the backbone in such a way that they can bind with a nucleic acid having a sequence of bases that are complementary to the bases of the oligonucleotide. The most common oligonucleotides have a backbone of sugar phosphate units. A distinction may be made between oligodeoxyribonucleotides that do not have a hydroxyl group at the 2' position and oligoribonucleotides that have a hydroxyl group at the 2' position. Oligonucleotides may also include derivatives, in which the hydrogen of the hydroxyl group is replaced with organic groups, e.g., an allyl group. Oligonucleotides that function as primers or probes are generally at least about 10-15 nucleotides in length, or up to about 70, 100, 110, 150 or 200 nucleotides in length, and more preferably at least about 15 to 25 nucleotides in length. Oligonucleotides used as primers or probes for specifically amplifying or specifically detecting a particular target nucleic acid generally are capable of specifically hybridizing to the target nucleic acid.

As used herein, the term "primer" refers to an oligonucleotide, which is capable of acting as a point of initiation of nucleic acid sequence synthesis when placed under conditions in which synthesis of a primer extension product which is complementary to a target nucleic acid strand is induced, i.e., in the presence of different nucleotide triphosphates and a polymerase in an appropriate buffer ("buffer" includes pH, ionic strength, cofactors etc.) and at a suitable temperature. One or more of the nucleotides of the primer can be modified for instance by addition of a methyl group, a biotin or digoxigenin moiety, a fluorescent tag or by using radioactive nucleotides. A primer sequence need not reflect the exact sequence of the template. For example, a non-complementary nucleotide fragment may be attached to the 5' end of the primer, with the remainder of the primer sequence being substantially complementary to the strand. The term primer as used herein includes all forms of primers that may be synthesized including peptide nucleic acid primers, locked nucleic acid primers, phosphorothioate modified primers, labeled primers, and the like. The term "forward primer" as used herein means a primer that anneals to the anti-sense strand of double-stranded DNA (dsDNA). A "reverse primer" anneals to the sense-strand of dsDNA.

Primers are typically at least 10, 15, 18, or 30 nucleotides in length or up to about 100, 110, 125, or 200 nucleotides in length. In some embodiments, primers are preferably between about 15 to about 60 nucleotides in length, and most preferably between about 25 to about 40 nucleotides in length. In some embodiments, primers are 15 to 35 nucleotides in length. There is no standard length for optimal hybridization or polymerase chain reaction amplification. An optimal length for a particular primer application may be readily determined in the manner described in H. Erlich, PCR *Technology*, PRINCIPLES AND APPLICATION FOR DNA AMPLIFICATION, (1989).

As used herein, the term "primer pair" refers to a forward and reverse primer pair (i.e., a left and right primer pair) that can be used together to amplify a given region of a nucleic acid of interest.

"Probe" as used herein refers to a nucleic acid that interacts with a target nucleic acid via hybridization. A probe may be fully complementary to a target nucleic acid sequence or partially complementary. The level of complementarity will depend on many factors based, in general, on the function of the probe. Probes can be labeled or unlabeled, or modified in any of a number of ways well known in the art. A probe may specifically hybridize to a target nucleic acid. Probes may be DNA, RNA or a RNA/DNA hybrid. Probes may be oligonucleotides, artificial chromosomes, fragmented artificial chromosome, genomic nucleic acid, fragmented genomic nucleic acid, RNA, recombinant nucleic acid, fragmented recombinant nucleic acid, peptide nucleic acid (PNA), locked nucleic acid, oligomer of cyclic heterocycles, or conjugates of nucleic acid. Probes may comprise modified nucleobases, modified sugar moieties, and modified internucleotide linkages. Probes are typically at least about 10, 15, 20, 25, 30, 35, 40, 50, 60, 75, 100 nucleotides or more in length.

As used herein, the term "sample" refers to clinical samples obtained from a patient. In preferred embodiments, a sample is obtained from a biological source (i.e., a "biological sample"), such as tissue or bodily fluid collected from a subject. Sample sources include, but are not limited to, mucus, sputum (processed or unprocessed), bronchial alveolar lavage (BAL), bronchial wash (BW), blood, bodily fluids, cerebrospinal fluid (CSF), urine, plasma, serum, or tissue (e.g., biopsy material). Preferred sample sources include plasma, serum, or whole blood.

A "sample CFTR nucleic acid" is a CFTR nucleic acid in, or isolated from, a biological sample. Processing methods to release or otherwise make available a nucleic acid for detection are well known in the art and may include steps of nucleic acid manipulation, e.g., DNA or RNA extraction from a biological sample, and preparing a cDNA by reverse transcription of RNA from the biological sample. A biological sample may be a body fluid or a tissue sample. In some embodiments, a biological sample may comprise blood, plasma, sera, urine, feces, epidermal sample, vaginal sample, skin sample, cheek swab, sperm, amniotic fluid, cultured cells, bone marrow sample and/or chorionic villi, cultured cells, and the like. In some embodiments, the biological sample may be a dried biological fluid sample collected by a volumetric absorptive microsampling device. Fixed or frozen tissues also may be used. Amniotic fluid of 10-15 ml, cultured cells which are 80-100% confluent in two T-25 flasks and 25 mg of chorionic villi are useful sample amounts for processing.

The term "sensitivity," as used herein in reference to the methods of the present technology, is a measure of the ability of a method to detect a preselected sequence variant in a heterogeneous population of sequences. A method has a sensitivity of S % for variants of F % if, given a sample in which the preselected sequence variant is present as at least F % of the sequences in the sample, the method can detect the preselected sequence at a preselected confidence of C %, S % of the time. By way of example, a method has a sensitivity of 90% for variants of 5% if, given a sample in which the preselected variant sequence is present as at least 5% of the sequences in the sample, the method can detect the preselected sequence at a preselected confidence of 99%, 9 out of 10 times (F=5%; C=99%; S=90%). Exemplary sensitivities include at least 50, 60, 70, 80, 90, 95, 98, and 99%.

"Sequencing depth" or "read depth" as used herein refers to the number of times a sequence has been sequenced (the depth of sequencing). As an example, read depth can be determined by aligning multiple sequencing run results and counting the start position of reads in nonoverlapping windows of a certain size (for example, 100 bp). Copy number variation can be determined based on read depth using methods known in the art, for example, the methods described in Yoon et al., *Genome Research* September; 19(9):1586-1592 (2009); Xie et al., *BMC Bioinformatics* 10:80 (2009); or Medvedev et al., *Nature Methods* 6(11 Suppl):513-20 (2009). Use of this type of method and analysis is referred to as a "read depth approach."

The term "specific" as used herein in reference to an oligonucleotide primer means that the nucleotide sequence of the primer has at least 12 bases of sequence identity with a portion of the nucleic acid to be amplified when the oligonucleotide and the nucleic acid are aligned. An oligonucleotide primer that is specific for a nucleic acid is one that, under the stringent hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 85-95%, and more preferably at least 98% sequence identity. Sequence identity can be determined using a commercially available computer program with a default setting that employs algorithms well known in the art. As used herein, sequences that have "high sequence identity" have identical nucleotides at least at about 50% of aligned nucleotide positions, preferably at least at about 60% of aligned nucleotide positions, and more preferably at least at about 75% of aligned nucleotide positions.

"Specificity," as used herein, is a measure of the ability of a method to distinguish a truly occurring preselected sequence variant from sequencing artifacts or other closely related sequences. It is the ability to avoid false positive detections. False positive detections can arise from errors introduced into the sequence of interest during sample preparation, sequencing error, or inadvertent sequencing of closely related sequences like pseudo-genes or members of a gene family. A method has a specificity of X % if, when applied to a sample set of $N_{Total}$ sequences, in which $X_{True}$ sequences are truly variant and $X_{Not\ true}$ are not truly variant, the method selects at least X % of the not truly variant as not variant. E.g., a method has a specificity of 90% if, when applied to a sample set of 1,000 sequences, in which 500 sequences are truly variant and 500 are not truly variant, the method selects 90% of the 500 not truly variant sequences as not variant. Exemplary specificities include at least 50, 60, 70, 80, 90, 95, 98, and 99%.

The term "stringent hybridization conditions" as used herein refers to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5×Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

The terms "target nucleic acid" or "target sequence" or "target segment" as used herein refer to a nucleic acid sequence of interest to be detected and/or quantified in the sample to be analyzed. Target nucleic acid may be composed of segments of a chromosome, a complete gene with or without intergenic sequence, segments or portions of a gene with or without intergenic sequence, or sequence of nucleic acids which probes or primers are designed. Target nucleic acids may include a wild-type sequence(s), a mutation, deletion, insertion or duplication, tandem repeat elements, a gene of interest, a region of a gene of interest or any upstream or downstream region thereof. Target nucleic acids may represent alternative sequences or alleles of a particular gene. Target nucleic acids may be derived from genomic DNA, cDNA, or RNA.

As used herein, the terms "treat," "treating" or "treatment" refer, to an action to obtain a beneficial or desired clinical result including, but not limited to, alleviation or amelioration of one or more signs or symptoms of a disease or condition (e.g., regression, partial or complete), diminishing the extent of disease, stability (i.e., not worsening, achieving stable disease) state of disease, amelioration or palliation of the disease state, diminishing rate of or time to progression, and remission (whether partial or total).

Microsampling Devices Employed in the Methods of the Present Technology

Conventional dried blood spotting techniques are accompanied by a number of drawbacks, including imprecise sample volume and reliance on a constant sample viscosity (i.e., the expectation that the sample will spread uniformly on the sample card). A constant viscosity results in blood spot diameters remaining constant when equal volume samples are administered to the cards. However, viscosity varies significantly between blood samples because of differing hematocrit (HCT) or packed cell volume (PCV) levels in the blood. Samples with high hematocrit levels form smaller diameter spots on the bloodspot papers, leading to different concentrations of blood within the fixed diameter of the spots sampled. PCV levels are believed to show a variance of about 45% in spot diameters. As internal standards are sprayed onto the spotted blood, this can result in a 45% error in quantitation. The microsampling devices employed in the methods disclosed herein confer several advantages, including the collection of more precise blood volumes, lack of hematocrit bias, and the ability to be easily automated with standard liquid handlers for lab processing.

Additionally, conventional blood spot techniques require a comparatively large volume of blood relative to the disclosed microsampling devices. A dried blood spot would generally require 50-75 µl per spot, while a microsampling device can yield results from approximately 20 µl. It has been recognized in the art that dried blood spots often have performance variability issues for detecting viral load compared to other samples types, such as plasma (Pannus et al., *Medicine*, 95:48(e5475) (2016)), and the volume of a dried blood spot may need to be significantly higher for certain types of assessment (e.g., optical density) compared to other sample types, such as serum (Brandao et al., *J. Clin. Virol.*, 57:98-102 (2013)). Indeed, found that using both dried blood spot and plasma spot screening for detecting viral load and treatment failure in HIV patients receiving antiretroviral therapy found that both yielded a high rate of false positives (Sawadogo et al., J. Clin. Microbiol., 52(11):3878-83 (2014)).

The microsampling device useful in the methods of the present technology comprises an absorbent tip having a distal end and a proximal end. The width of the distal end of the absorbent tip is narrow compared to the width of the proximal end. The proximal end is attached to a holder, whereas the distal end is configured to contact a fluid to be absorbed, such as blood. The microsampling device permits biological fluid samples, such as blood, to be easily dried, shipped, and then later analyzed. In certain embodiments, the biological fluid is blood from a fingerstick.

Wicking action draws the blood into the absorbent tip. An optional barrier between the absorbent tip and the holder prevents blood from passing or wicking to the holder. The absorbent tip is composed of a material that wicks up substantially the same volume of fluid even when excess fluid is available (volumetric absorptive microsampling or VAMS™). The volume of the absorbent tip affects the volume of fluid absorbed. The size and shape of the absorbent tip may be varied to adjust the volume of absorbed blood and the rate of absorption. Blood volumes of about 7-15 µL, about 20 µL, and even up to about 30 µL may be acceptable. The sampling time may be about 2 seconds, about 3 seconds, about 5 seconds, or up to about 10 seconds.

In some embodiments, the material used for the absorbent tip is hydrophilic (e.g., polyester). Alternatively, the material may initially be hydrophobic and is subsequently treated to make it hydrophilic. Hydrophobic matrices may be rendered hydrophilic by a variety of known methods, such as plasma treatment or surfactant treatment (e.g., Tween-40 or Tween-80) of the matrix. In some embodiments, plasma treatment is used to render a hydrophobic material such as polyolefin, e.g., polyethylene, hydrophilic. Alternatively, the grafting of hydrophilic polymers to the surface and the chemical functionalization of active groups on the surface with polar or hydrophilic molecules such as sugars can be used to achieve a hydrophilic surface for the absorbent tip. Covalent modification could also be used to add polar or hydrophilic functional groups to the surface of absorbent tip. Other suitable materials for the absorbent tip include sintered glass, sintered steel, sintered ceramics, and sintered polymers of plastic, and sintered polyethylene.

In some embodiments, the microsampling device comprises an absorbent tip made of a hydrophilic polymeric material of sufficient size to absorb a maximum of about 20 µL of blood in about 2-5 seconds, and having a length of less than about 5 mm (0.2 inches) and a cross-sectional area of less than about 20 mm$^2$ and a density of less than about 4 g/cc. In some embodiments, the absorbent tips are composed of polyethylene and configured to absorb about 1-20 microliters of blood, preferably within 1-7 seconds, and more preferably within about 1-5 seconds. The absorbent tip may contain one or more of dried blood, dried anticoagulant or an internal standard.

In certain embodiments, the absorbent tips have a volume of about 35 mm$^3$, absorb about 13-14 microliters of blood in about 3 seconds, absorb 9-10 microliters of blood in about 2.5 seconds, and have a pore volume of about 38%. In other embodiments, the absorbent tips have a volume of about 24 microliters, a density of about 0.6 g/cc, absorb about 10 microliters of blood in about 2.5 seconds, and have a pore volume of about 40%. In some embodiments, the volumetric absorptive microsampling device is a MITRA® tip, as described in US 2013/0116597, which is herein incorporated by reference in its entirety.

The absorbent tip may be shaped with an exterior resembling a truncated cone with a narrow and rounded distal end. In some embodiments, the holder has a cylindrical post that fits into a recess inside the center of the absorbent tip and extending along the longitudinal axis of the absorbent tip and holder. The conical shape of the absorbent tip helps wick the sample quickly and uniformly.

The holder may be adapted for use with a pipette. In some embodiments, a tubular, conical shaped holder is preferred, with the absorbent tip on the narrow end of the holder. The wider opposite end of the holder may be closed, or open and hollow, and may optionally be configured to attach to a pipette tip. The holder may have outwardly extending flanges that are arranged to abut mating structures in holders, drying racks or test equipment to help position the absorbent tip at desired locations in such holders, drying racks and test equipment.

In certain embodiments, the holder may include a pipette tip or a tapering, tubular structure configured to nest with a pipette tip. The absorbent tip may be composed of polyethylene, and both the absorbent tip and holder are made under aseptic conditions, or are terminally sterilized. The absorbent tip may contain dried anti-coagulant. In some embodiments, the holder has a plurality of ribs extending along a length of the holder. The ribs may have a height and length selected to keep the absorbent tip from contacting walls of a recess into which the holder and absorbent tip are placed for shipment, or for extraction of the dried blood in the absorbent tip.

After absorbing a small-volume sample, the absorbent tip is then dried. In some embodiments, the small-volume blood sample is dried for at least 10 minutes, at least 20 minutes, at least 30 minutes, at least 40 minutes, at least 50 minutes, at least 1 hour, at least 2 hours, at least 3 hours, at least 4 hours, at least 5 hours, at least 6 hours, at least 8 hours, at least 12 hours, at least 16 hours, at least 20 hours, at least 24 hours, at least 48 hours, at least 72 hours, or at least 96 hours at ambient or room temperature. In certain embodiments, the small-volume blood sample is dried for about 2-3 hours.

Drying can be done on a suitable rack or holder, or preferably the absorbent tip and holder can be transferred to a special drying container configured to facilitate drying while minimizing contact between the absorbent tip and the walls of the drying container or other potential contaminant surfaces. The drying container may have a desiccant to facilitate drying. The drying container may also provide a protective cover which may be sealed for transport to prevent contamination. In some embodiments, the cover has a surface onto which printed indicia may be written to identify the source of the dried blood sample and provide other relevant information. In some embodiments, the dimensions of the container, and the relative positions of the holders within the container, will conform to SBS Microwell plate specifications. The microsampling device and the drying container may be placed in a plastic bag along with a desiccant to assist with drying and can either be shipped in this fashion, or shipped after the desiccant is removed.

In some embodiments, the wider opposite end of the holder is hollow and the container has a first portion with a mounting projection portion sized to fit into and releasably engage the hollow end of the holder. Additionally or alternatively, the container has a second portion releasably fastened to the first portion and has a recess configured to enclose a portion of the holder for transportation of the holder. The container may comprise a plurality of openings allowing air to access the absorbent tip of the microsampling device. Moreover, the first portion may have a side with an access port therein of sufficient size and located so that indicia may be applied through the port and onto the holder when the holder is on the mounting projection.

Upon receipt at the testing location, the absorbent tip may be eluted in a predetermined volume of a suitable buffer (as described herein) either manually or via automated means to extract the nucleic acids or proteins of interest from dried blood. Physical agitation techniques such as sonication or vortexing of the fluid and/or the absorbent tip may accelerate the extraction process from the dried blood into a liquid sample matrix. Physical separation techniques such as centrifugation, evaporation/reconstitution, concentration, precipitation, liquid/liquid extraction, and solid phase extraction can be used to further simplify the sample matrix for further analysis.

Each container may enclose a plurality of holders, wherein each holder comprises an absorbent tip at its distal end and has a hollow proximal end. The container likewise has a plurality of elongated mounting projections each sized to fit into and releasably engage the hollow ends of the plurality of holders. The second portion of the container has recesses configured to separately enclose each of the plurality of holders in a separate enclosure within the container. In certain embodiments, each of the plurality of holders has a plurality of ribs extending along a length of the holder with the ribs configured to keep the absorbent tip from contacting walls of the container. As desired, a desiccant may be placed inside the container to help dry the blood in the absorbent tip or maintain dryness. Each holder may have visible indicia associating the holder with the container and with at least one other holder, such as serial numbers with various portions of the number indicating related holders/absorbent tips and the container in which the holders are shipped.

Nucleic Acid Extraction

In one aspect, the present disclosure provides a method for extracting genomic DNA from a dried biological fluid sample collected with a volumetric absorptive microsampling device (e.g., MITRA® Tip). In some embodiments, the dried biological fluid sample is eluted by contacting the absorbent tip of a volumetric absorptive microsampling device with a lysis buffer and proteinase K. The lysis buffer may comprise guanidine hydrochloride, Tris.Cl, EDTA, Tween 20, and Triton X-100. Proteinase K is a broad spectrum serine protease that is stable over a wide pH range (4-12), with a pH optimum of pH 8.0. The predominant site of Proteinase K cleavage is the peptide bond adjacent to the carboxyl group of aliphatic and aromatic amino acids with blocked alpha amino groups. Elevating the reaction temperature from 37° C. to 50-60° C. may increase the Proteinase K activity by several fold. Proteinase K activity can be enhanced by the addition of 0.5-1% sodium dodecyl sulfate (SDS), 3 M Guanidinium chloride, 1 M Guanidinium thiocyanate, or 4 M urea.

Alternatively, other protocols for nucleic acid extraction may be used in the methods of the present technology. Examples of other commercially available nucleic acid purification kits include Molzym GmbH & Co KG (Bremen, D E), Qiagen (Hilden, D E), Macherey-Nagel (Düren, D E), Roche (Basel, C H) or Sigma (Deisenhofen, D E). Other systems for nucleic acid purification, which are based on the use of polystyrene beads etc., as support material may also be used.

In some embodiments, extraction of genomic DNA from a dried biological fluid sample collected with a volumetric absorptive microsampling device comprises denaturing nucleoprotein complexes in cells present in the dried biological fluid sample. In certain embodiments, extraction of genomic DNA from a dried biological fluid sample collected with a volumetric absorptive microsampling device comprises removing protein contaminants, inactivating nuclease activity, and/or removing biological and/or chemical contaminants present in the dried biological fluid sample.

In some embodiments, extraction of genomic DNA from a dried biological fluid sample collected with a volumetric absorptive microsampling device may be performed using automated DNA extraction platforms. In some embodiments, the automated DNA extraction platform has high-throughput capacity, such as up to 100 extractions per cycle. In certain embodiments, extraction of genomic DNA from a dried biological fluid sample collected with a volumetric absorptive microsampling device may be performed using commercially available automated workstations, such as the QIAsymphony® or Hamilton® automation. In some embodiments, extraction of genomic DNA from a dried biological fluid sample collected with a volumetric absorptive microsampling device is performed on an EZ1 Advanced XL, EZ1 Advanced, or Biorobot® EZ1™ automated system with an EZ1 DNA Investigator Kit. In some embodiments, extraction of genomic DNA from a dried biological fluid sample collected with a volumetric absorptive microsampling device is performed using commercially available reagent kits.

NGS Platforms

In some embodiments, high throughput, massively parallel sequencing employs sequencing-by-synthesis with reversible dye terminators. In other embodiments, sequencing is performed via sequencing-by-ligation. In yet other embodiments, sequencing is single molecule sequencing. Examples of Next Generation Sequencing techniques include, but are not limited to pyrosequencing, Reversible dye-terminator sequencing, SOLiD sequencing, Ion semiconductor sequencing, Helioscope single molecule sequencing etc.

The Ion Torrent™ (Life Technologies, Carlsbad, Calif.) amplicon sequencing system employs a flow-based approach that detects pH changes caused by the release of hydrogen ions during incorporation of unmodified nucleotides in DNA replication. For use with this system, a sequencing library is initially produced by generating DNA fragments flanked by sequencing adapters. In some embodiments, these fragments can be clonally amplified on particles by emulsion PCR. The particles with the amplified template are then placed in a silicon semiconductor sequencing chip. During replication, the chip is flooded with one nucleotide after another, and if a nucleotide complements the DNA molecule in a particular microwell of the chip, then it will be incorporated. A proton is naturally released when a nucleotide is incorporated by the polymerase in the DNA molecule, resulting in a detectable local change of pH. The pH of the solution then changes in that well and is detected by the ion sensor. If homopolymer repeats are present in the template sequence, multiple nucleotides will be incorporated in a single cycle. This leads to a corresponding number of released hydrogens and a proportionally higher electronic signal.

The 454™ GS FLX™ sequencing system (Roche, Germany), employs a light-based detection methodology in a large-scale parallel pyrosequencing system. Pyrosequencing uses DNA polymerization, adding one nucleotide species at a time and detecting and quantifying the number of nucleotides added to a given location through the light emitted by the release of attached pyrophosphates. For use with the 454™ system, adapter-ligated DNA fragments are fixed to small DNA-capture beads in a water-in-oil emulsion and amplified by PCR (emulsion PCR). Each DNA-bound bead is placed into a well on a picotiter plate and sequencing reagents are delivered across the wells of the plate. The four DNA nucleotides are added sequentially in a fixed order across the picotiter plate device during a sequencing run. During the nucleotide flow, millions of copies of DNA bound to each of the beads are sequenced in parallel. When a nucleotide complementary to the template strand is added to a well, the nucleotide is incorporated onto the existing DNA strand, generating a light signal that is recorded by a CCD camera in the instrument.

Sequencing technology based on reversible dye-terminators: DNA molecules are first attached to primers on a slide and amplified so that local clonal colonies are formed. Four types of reversible terminator bases (RT-bases) are added, and non-incorporated nucleotides are washed away. Unlike pyrosequencing, the DNA can only be extended one nucleotide at a time. A camera takes images of the fluorescently labeled nucleotides, then the dye along with the terminal 3' blocker is chemically removed from the DNA, allowing the next cycle.

Helicos's single-molecule sequencing uses DNA fragments with added polyA tail adapters, which are attached to the flow cell surface. At each cycle, DNA polymerase and a single species of fluorescently labeled nucleotide are added, resulting in template-dependent extension of the surface-immobilized primer-template duplexes. The reads are performed by the Helioscope sequencer. After acquisition of images tiling the full array, chemical cleavage and release of the fluorescent label permits the subsequent cycle of extension and imaging.

Sequencing by synthesis (SBS), like the "old style" dye-termination electrophoretic sequencing, relies on incorporation of nucleotides by a DNA polymerase to determine the base sequence. A DNA library with affixed adapters is denatured into single strands and grafted to a flow cell, followed by bridge amplification to form a high-density array of spots onto a glass chip. Reversible terminator methods use reversible versions of dye-terminators, adding one nucleotide at a time, detecting fluorescence at each position by repeated removal of the blocking group to allow polymerization of another nucleotide. The signal of nucleotide incorporation can vary with fluorescently labeled nucleotides, phosphate-driven light reactions and hydrogen ion sensing having all been used. Examples of SBS platforms include Illumina GA, HiSeq 2500, HiSeq 1500, HiSeq 2000, or HiSeq 1000. The MiSeq® personal sequencing system (Illumina, Inc.) also employs sequencing by synthesis with reversible terminator chemistry.

In contrast to the sequencing by synthesis method, the sequencing by ligation method uses a DNA ligase to determine the target sequence. This sequencing method relies on enzymatic ligation of oligonucleotides that are adjacent through local complementarity on a template DNA strand. This technology employs a partition of all possible oligonucleotides of a fixed length, labeled according to the sequenced position. Oligonucleotides are annealed and ligated and the preferential ligation by DNA ligase for matching sequences results in a dinucleotide encoded color space signal at that position (through the release of a fluorescently labeled probe that corresponds to a known nucleotide at a known position along the oligo). This method is primarily used by Life Technologies' SOLiD™ sequencers. Before sequencing, the DNA is amplified by emulsion PCR. The resulting beads, each containing only copies of the same DNA molecule, are deposited on a solid planar substrate.

SMRT™ sequencing is based on the sequencing by synthesis approach. The DNA is synthesized in zero-mode wave-guides (ZMWs)—small well-like containers with the capturing tools located at the bottom of the well. The sequencing is performed with use of unmodified polymerase (attached to the ZMW bottom) and fluorescently labeled nucleotides flowing freely in the solution. The wells are constructed in a way that only the fluorescence occurring at the bottom of the well is detected. The fluorescent label is detached from the nucleotide at its incorporation into the DNA strand, leaving an unmodified DNA strand.

High-throughput sequencing of DNA can also take place using AnyDot-chips (Genovoxx, Germany), which allows monitoring of biological processes (e.g., miRNA expression or allele variability (SNP detection)). For example, the AnyDot-chips allow for 10x-50x enhancement of nucleotide fluorescence signal detection. Other high-throughput sequencing systems include those disclosed in Venter, J., et al., Science 16 Feb. 2001; Adams, M. et al., Science 24 Mar. 2000; and M. J, Levene, et al., Science 299:682-686, January 2003; as well as U.S. Application Pub. No. 2003/0044781 and 2006/0078937.

Cystic Fibrosis Detection Assays of the Present Technology

Provided herein are methods for detecting at least one mutation in a sample CFTR nucleic acid comprising generating a library comprising amplicons corresponding to a plurality of target segments of the sample CFTR nucleic acid, wherein the sample CFTR nucleic acid is extracted from a dried biological fluid sample eluted from an absorbent tip of a microsampling device (e.g., MITRA® Tip) with a lysis buffer and Proteinase K. In some embodiments, the at least one mutation in the sample CFTR nucleic acid is selected from among a base change, a gene deletion and a gene duplication. In certain embodiments, the at least one mutation in the sample CFTR nucleic acid is associated with cystic fibrosis, and comprises one or more of the mutations listed in Table 2 of the present disclosure. In some embodiments, the at least one mutation of the sample CFTR nucleic acid is detected using high throughput massive parallel sequencing. In some embodiments, the lysis buffer comprises guanidine hydrochloride, Tris.Cl, EDTA, Tween 20, and Triton X-100.

In some embodiments, the dried biological fluid sample is dried plasma, dried serum, or dried whole blood. In certain embodiments, the dried biological fluid sample is obtained from a patient exhibiting cystic fibrosis symptoms, or has a family history of cystic fibrosis or a CFTR mutation. In some embodiments, the dried biological fluid sample is obtained from a male partner of an obstetrics and gynecology patient having cystic fibrosis or at least one CFTR mutation. In some embodiments, the dried biological fluid sample is obtained from an patient who is unable to provide large volumes of blood for recurrent testing, such as an infant or an elderly person.

In some embodiments, the dried biological fluid sample on the absorbent tip of the microsampling device is collected from a patient via fingerstick. In certain embodiments, the microsampling device is a MITRA® tip. Elution of the dried biological fluid sample may be performed by contacting the absorbent tip of the microsampling device with a lysis buffer and Proteinase K. In certain embodiments, the lysis buffer comprises guanidine hydrochloride, Tris.Cl, EDTA, Tween 20, and Triton X-100. In a further embodiment, the lysis buffer comprises 800 mM guanidine hydrochloride; 30 mM Tris.Cl, pH 8.0; 30 mM EDTA, pH 8.0; 5% Tween 20; and 0.5% Triton X-100.

Additionally or alternatively, in some embodiments, elution of the dried biological fluid sample is performed by contacting the absorbent tip of the microsampling device with the lysis buffer for up to 15 minutes at 90° C. Additionally or alternatively, in certain embodiments, elution of the dried biological fluid sample is performed by contacting the absorbent tip of the microsampling device with Proteinase K for up to 1 hour at 56° C. In other embodiments, elution of the dried biological fluid sample is performed by contacting the absorbent tip of the microsampling device with Proteinase K for up to 16-18 hours at 56° C. In some embodiments, the sample volume of the microsampling device is no more than 10-20 µL.

In some embodiments of the method, no more than 400 ng of genomic DNA is eluted from the absorbent tip of the microsampling device. In other embodiments of the method, about 100 ng to about 400 ng of genomic DNA is eluted from the absorbent tip of the microsampling device. In some embodiments, the method further comprises ligating an adapter sequence to the ends of the plurality of amplicons. The adapter sequence may be a P5 adapter, P7 adapter, P1 adapter, A adapter, or Ion Xpress™ barcode adapter. Additionally or alternatively, in some embodiments, the method further comprises hybridizing one or more bait sequences to one or more target segments of the sample CFTR nucleic acid.

In certain embodiments, the CFTR target segment that is amplified and sequenced according to the present technology may represent one or more individual exon(s) or portion(s) of exon(s) of the CFTR gene or one or more portions of a CFTR mRNA or cDNA. A target segment also may include the CFTR promoter region and/or one or more CFTR introns. In some embodiments, the target segments represent the entire CFTR gene or the entire CFTR coding region. In some embodiments, the target segments represent the entire CFTR coding region and at least one intron or a portion thereof, and an adjacent region located immediately upstream (in the 5' direction) of the coding sequence. The adjacent, upstream region may comprise from about 100 nucleotides up to about 500, 750, 1000, 1100, or 1200 nucleotides of the sequence located immediately upstream of the CFTR coding sequence. In some embodiments, the adjacent, upstream region comprises all or a portion of the CFTR promoter sequence. In some embodiments, the sample CFTR nucleic acid is genomic DNA.

In another aspect, the present disclosure provides a method for detecting at least one mutation in a sample CFTR nucleic acid comprising generating a library comprising amplicons corresponding to a plurality of target segments of the sample CFTR nucleic acid, wherein the sample CFTR nucleic acid is extracted from a dried biological fluid sample eluted from an absorbent tip of a microsampling device with a lysis buffer and Proteinase K, and detecting the at least one mutation in the sample CFTR nucleic acid using high throughput massive parallel sequencing. In some embodiments, the lysis buffer comprises guanidine hydrochloride, Tris.Cl, EDTA, Tween 20, and Triton X-100.

Additionally or alternatively, in some embodiments, the plurality of target segments of the sample CFTR nucleic acid comprise at least one alteration compared to the corresponding region of a reference CFTR nucleotide sequence. A reference CFTR nucleotide sequence may be a CFTR genomic or cDNA sequence, or a portion thereof, from a normal (non-cystic fibrosis afflicted and non-cystic fibrosis carrier) individual. In some cases, a reference CFTR sequence may comprise a wild-type CFTR nucleic acid sequence. Various methods known in the art (e.g., read depth approach) can be employed to analyze sequencing data to determine if differences are present in the sample CFTR nucleic acid sequence compared to a reference CFTR nucleic acid sequence.

In some embodiments, the at least one mutation in the sample CFTR nucleic acid is selected from a base change, a gene deletion and a gene duplication. In some embodiments, the at least one mutation in the sample CFTR nucleic acid is associated with cystic fibrosis, and may include more or more mutations disclosed in Table 2.

In some embodiments, the methods disclosed herein can be used to detect one or more rare CFTR mutations or private mutations in a CFTR sample nucleic acid obtained from an individual, thereby identifying an individual who possesses one or more rare or private CFTR mutation(s). In some embodiments, the methods of the present technology are used to identify rare familial mutations in an obligate cystic fibrosis carrier after the carrier has tested negative in a routine screening test for common mutations. Such routine screening tests may include CF Mutation Screen (Quest Diagnostics), CFTR Screen, Cystic Fibrosis Screen (Quest Diagnostics), and Cystic Fibrosis Carrier Screen (LabCorp). In some embodiments, the present methods can also be used to identify rare mutations in a cystic fibrosis-affected (i.e. symptomatic) individual who has not had two CFTR sequence mutations identified by at least one routine cystic fibrosis mutation screening test.

In one aspect, the present disclosure provides a method for detecting a genetic basis for being affected with cystic fibrosis, or for being a cystic fibrosis carrier in an individual comprising: (a) generating an amplicon library by amplifying multiple target segments of a CFTR nucleic acid obtained from the individual, wherein the sample CFTR nucleic acid is extracted from a dried biological fluid sample eluted from an absorbent tip of a microsampling device; (b) sequencing the amplicons in the amplicon library using high throughput massive parallel sequencing, and (c) detecting a genetic basis for being affected with cystic fibrosis, or for being a cystic fibrosis carrier when the nucleotide sequence of one or more of the target segments of the CFTR nucleic acid comprises a mutation associated with cystic fibrosis.

In some embodiments, the methods disclosed herein are employed to confirm cystic fibrosis carrier status in an individual such as, for example, a parent, a sibling or other relatives of a cystic fibrosis-affected individual with one or more rare or private mutations. In some embodiments, the at least one mutation is associated with cystic fibrosis, and includes one or more mutations disclosed in Table 2. Both gene sequence and gene dosage may be determined in a nucleic acid sample using the methods disclosed herein. Gene dosage (also referred to as copy number variation or CNVs) can be determined by performing next generation sequencing and using a read depth approach. CNVs are gains and losses of genomic sequence >50 bp between two individuals of a species (Mills et al., Nature 470: 59-65 (2011)). A normal dosage in relation to all other amplicons for a normal specimen will be one, ½ for a homozygous deletion and 1½ for a homozygous duplication.

In some embodiments, at least 2, 5, 10, 20, 25, or 28 and up to 25, 29, or 30, target segments of the CFTR gene may be sequenced with gains and losses of genomic sequence (>50 bp) determined using a read depth approach. In one embodiment, 29 target segments are sequenced, representing the CFTR coding region (including all exons/intron junctions). In another embodiment, the CFTR coding region (including all exons/intron junctions) in addition to about 1 kb upstream and about 300 kb downstream of the CFTR gene are assayed.

Additionally or alternatively, in some embodiments, each CFTR nucleic acid target segment may be amplified with an oligonucleotide primer or primer pair specific to the target segment. In some embodiments a single primer or both primers of a primer pair comprise a specific adapter sequence (also referred to as a sequencing adapter) ligated to the 5' end of the target specific sequence portion of the primer. This sequencing adapter is a short oligonucleotide of known sequence that can provide a priming site for both amplification and sequencing of the adjoining, unknown nucleic acid. As such, adapters allow binding of a fragment to a flow cell for next generation sequencing. Any adapter sequence may be included in a primer used in the present technology. In some embodiments, the amplicons corresponding to the plurality of target segments of the sample CFTR nucleic acid are generated using primers that contain an oligonucleotide sequencing adapter to produce adapter tagged amplicons. In other embodiments, the employed primers do not contain adapter sequences and the amplicons produced are subsequently (i.e. after amplification) ligated to an oligonucleotide sequencing adapter on one or both ends of the amplicons.

In some embodiments, all forward amplicons (i.e., amplicons extended from forward primers that hybridized with antisense strands of a target segment) contain the same adapter sequence. In some embodiments when double stranded sequencing is performed, all forward amplicons contain the same adapter sequence and all reverse amplicons (i.e., amplicons extended from reverse primers that hybridized with sense strands of a target segment) contain an adapter sequence that is different from the adapter sequence of the forward amplicons. In some embodiments, the adapter sequences further comprise an index sequence (also referred to as an index tag, a "barcode" or a multiplex identifier (MID)).

In some embodiments, the adapter sequences are P5 and/or P7 adapter sequences that are recommended for Illumina sequencers (MiSeq and HiSeq). See, e.g., Williams-Carrier et al., *Plant J.,* 63(1):167-77 (2010). In some embodiments, the adapter sequences are P1, A, or Ion Xpress™ barcode adapter sequences that are recommended for Life Technologies sequencers. Other adapter sequences are known in the art. Some manufacturers recommend specific adapter sequences for use with the particular sequencing technology and machinery that they offer.

Additionally or alternatively, in some embodiments, the amplicons corresponding to the plurality of target segments of the sample CFTR nucleic acid from more than one sample are sequenced. In some embodiments, all samples are sequenced simultaneously in parallel. In any of the above embodiments, the amplicons corresponding to the plurality of target segments of the sample CFTR nucleic acid from at least 1, 5, 10, 20, 30 or up to 35, 40, 45, 48 or 50 different samples are amplified and sequenced using the methods described herein.

In some embodiments, amplicons derived from a single sample source further comprise an identical index sequence that indicates the source from which the amplicon is generated, the index sequence for each sample being different from the index sequences from all other samples. As such, the use of index sequences permits multiple samples to be pooled per sequencing run and the sample source subsequently ascertained based on the index sequence. In some embodiments, the Access Array™ System (Fluidigm Corp., San Francisco, Calif.) or the Apollo 324 System (Wafergen Biosystems, Fremont, Calif.) is used to generate a barcoded (indexed) amplicon library by simultaneously amplifying the nucleic acids from the samples in one set up.

In some embodiments, indexed amplicons are generated using primers (for example, forward primers and/or reverse primers) containing the index sequence. Such indexed primers may be included during library preparation as a "barcoding" tool to identify specific amplicons as originating from a particular sample source. When adapter-ligated and/or indexed primers are employed, the adapter sequence and/or index sequence gets incorporated into the amplicon (along with the target-specific primer sequence) during amplification. Therefore, the resulting amplicons are sequencing-competent and do not require the traditional library preparation protocol. Moreover, the presence of the index tag permits the differentiation of sequences from multiple sample sources.

In some embodiments, the amplicons may be amplified with non-adapter-ligated and/or non-indexed primers and a sequencing adapter and/or an index sequence may be subsequently ligated to one or both ends of each of the resulting amplicons. In some embodiments, the amplicon library is generated using a multiplexed PCR approach.

Indexed amplicons from more than one sample source are quantified individually and then pooled prior to high throughput sequencing. As such, the use of index sequences permits multiple samples (i.e., samples from more than one sample source) to be pooled per sequencing run and the sample source subsequently ascertained based on the index sequence. "Multiplexing" is the pooling of multiple adapter-tagged and indexed libraries into a single sequencing run. When indexed primer sets are used, this capability can be exploited for comparative studies. In some embodiments, amplicons from more than one sample source are pooled prior to high throughput sequencing. In some embodiments, amplicon libraries from up to 48 separate sources are pooled prior to sequencing.

In some embodiments, sequencing templates (amplicons) are prepared by emulsion-based clonal amplification of target segments using specialized fusion primers (containing an adapter sequence) and capture beads. A single adapter-bound fragment is attached to the surface of a bead, and an oil emulsion containing necessary amplification reagents is formed around the bead/fragment component. Parallel amplification of millions of beads with millions of single strand fragments produces a sequencer-ready library.

Additionally or alternatively, in some embodiments the amplicons constituting the adapter-tagged (and, optionally, indexed) amplicon library are produced by polymerase chain reaction (PCR). In some embodiments, the amplicon library is generated using a multiplexed PCR approach, such as that disclosed in U.S. Pat. No. 8,092,996, incorporated by reference herein in its entirety.

Bridge PCR is yet another method for in vitro clonal amplification after a library is generated, in preparation for sequencing. This process is a means to clonally amplify a single target molecule, a member of a library, in a defined physical region such as a solid surface, for example, a bead in suspension or a cluster on a glass slide. In this method, fragments are amplified using primers attached to the solid surface forming "DNA colonies" or "DNA clusters." This method is used in some of the genome analyzer sequencers manufactured by Illumina, Inc. (San Diego, Calif.).

Additionally or alternatively, in some embodiments, the plurality of amplicons are enriched using a bait set comprising nucleic acid sequences that are complementary to at least one of the plurality of amplicons. In some embodiments, the nucleic acid sequences of the bait set are RNA baits, DNA baits, or a combination thereof.

Following the production of an amplicon library, the amplicons are sequenced using high throughput, massive parallel sequencing (i.e. next generation sequencing). Methods for performing high throughput, massively parallel sequencing are known in the art. In certain embodiments, the high throughput massive parallel sequencing is performed using pyrosequencing, reversible dye-terminator sequencing, SOLiD sequencing, Ion semiconductor sequencing, Heliscope single molecule sequencing, sequencing by synthesis, sequencing by ligation, or SMRT™ sequencing.

Treatment of Cystic Fibrosis

Disclosed herein are methods for determining whether a patient will benefit from one or more treatment for cystic fibrosis.

Examples of treatment for cystic fibrosis are well known in the art and include therapies that control the infectious microbiome in a patient's system, such as treatment with antibiotics or anti-inflammatory medications, chest physical therapies (CPTs), airway clearance techniques (ACTs) and medications, nutrition therapies, organ transplantation (e.g., lung replacement surgery), etc.

Suitable antibiotics or combination of antibiotics may be used to treat infections associated with cystic fibrosis. Classes of antibiotics that are useful in the treatment of cystic fibrosis include Penicillins such as penicillin and amoxicillin, Cephalosporins such as cephalexin (Keflex), Macrolides such as erythromycin (E-Mycin), clarithromycin (Biaxin), and azithromycin (Zithromax), Fluoroquinolones such as ciprofolxacin (Cipro), levofloxacin (Levaquin), and ofloxacin (Floxin), Sulfonamides such as co-trimoxazole (Bactrim) and trimethoprim (Proloprim), Tetracyclines such as tetracycline (Sumycin, Panmycin) and doxycycline (Vibramycin), Aminoglycosides such as gentamicin (Garamycin) and tobramycin (Tobrex), and Colistin.

Anti-inflammatory medications may be used to reduce inflammation and pain caused by cystic fibrosis associated infections. Classes of anti-inflammatory medications include steroid-based anti-inflammatory agents, such as Amcinonide, Betamethosone diproprionate, Clobetasol, Clocortolone, Dexamethasone, Diflorasone, Dutasteride, Flumethasone Pivalate, Flunisolide, Fluocinolone Acetonide, Fluocinonide, Fluorometholone, Fluticasone propionate, Fluticasone propionate, Fluticasone propionate, Flurandrenolide and Hydroflumethiazide. Non-steroidal anti-inflammatory drugs (NSAIDs) include aceclofenac, acemetacin, aspirin, celecoxib, dexibuprofen, dexketoprofen, diclofenac, etodolac, etoricoxib, fenoprofen, flurbiprofen, ibuprofen, indometacin, ketoprofen, mefenamic acid, meloxicam, nabumetone, naproxen, sulindac, tenoxicam, and tiaprofenic acid.

Mucus thinning medications may be used to help keep a patient's lung and airway clear. Classes of mucus thinning medication include expectorants, antihistamines, and cough suppressants, such as Guaifenesin, Dextromethorphan, hypertonic salines, dornase alfa and mucolytics.

Chest physical therapies (CPTs) may involve chest clapping or percussion. Pounding a patient's chest and back repeatedly may help loosening and dislodging the mucus from the lungs so that the patient may cough up the mucus. In some cystic fibrosis therapeutic regimens, CPT is performed on the patient three to four times a day. In some cystic fibrosis therapeutic regimens, the patients may sit or lie on their stomach while CPT is performed to facilitate drainage of the mucus from the lungs. Certain devices may be used in CPT to reduce the patient's discomfort during the process. Exemplary devices include, but are not limited to, an electric chest clapper, an inflatable therapy vest that uses high-frequency air waves to force the mucus out of the lungs, a flutter device that a patient uses to breath out through, causing vibrations that dislodge the mucus, and a positive expiratory pressure mask that creates back pressure to help hold airways open, again facilitating dislodging of mucus from the airway walls.

Airway clearance techniques (ACTs) may help to loosen thick, sticky mucus so it can be cleared from patients' lungs by coughing or huffing. Clearing the airways may help decrease lung infections and improve lung function. Various ACTs are known and clinically performed. For example, coughing is a basic airway clearance technique. Coughing may be an involuntary reflex or can be controlled as a healthy, natural way for the lungs to eliminate mucus. Additionally, several breathing techniques may also help clear the patient's airway. Examples of these techniques include forced expiration technique (FET) which involves forcing out a couple of breaths of huffs followed by relaxed breathing; and active cycle breathing (ACB) that involves deep breathing exercises that can loosen the mucus and help open airways. In some cystic fibrosis therapeutic regimens, ACTs are used with other treatments, including inhaling medications that help relax airway wall muscles, and thin and dislodge mucus. Such medications may include but are not limited to bronchodilators, antibiotics, and mucus thinners. In some embodiments, medications are taken through a nebulizer during ACTs.

Nutritional therapy may be used alone or in combination with other therapies for treating cystic fibrosis. For example, a patient may receive pancreatic enzymes that aids in the digestion of fats and protein, and absorption of vitamins. Vitamin A, D, E, and K supplements may be administered to the patient to provide an additional source of fat-soluble vitamins. Feeding tubes such as a gastrostomy tube (G-tube), may be used to feed nutritional solutions directly to the patient's stomach. Medications or supplements that may reduce stomach acid may be administered concurrently with oral pancreatic enzymes. Other mucus thinners may be administered individually or concurrently to treat intestinal blockage as part of a nutritional therapy by correcting digestive problems.

In one aspect, the present disclosure provides a method for selecting a patient exhibiting cystic fibrosis symptoms, or a patient at risk for cystic fibrosis for treatment with an anti-cystic fibrosis therapeutic agent comprising (a) eluting a dried biological fluid sample of the patient from an absorbent tip of a microsampling device, wherein the dried biological fluid sample comprises a sample CFTR nucleic acid; (b) generating a library comprising amplicons corresponding to a plurality of target segments of the sample CFTR nucleic acid; (c) detecting at least one mutation in at least one of the amplicons in the library using high throughput massive parallel sequencing; and (d) selecting the patient for treatment with an anti-cystic fibrosis therapeutic agent. The dried biological fluid sample may be dried plasma, dried serum, or dried whole blood. In some embodiments, the microsampling device is a volumetric absorbent microsampling device. In certain embodiments, the dried biological fluid sample on the absorbent tip of the microsampling device is collected from a patient via fingerstick. In certain embodiments, the microsampling device is a MITRA® tip. In some embodiments, the patient harbors one or more mutations in the CFTR gene and may include one or more mutations listed in Table 2.

Patients at risk for cystic fibrosis include subjects having: (a) a genetic basis for cystic fibrosis; (b) at least one parent or at least one grandparent having a genetic basis for cystic fibrosis, such as being a cystic fibrosis carrier; (c) familial incidences of cystic fibrosis in multiple generations; or (d) one or more symptoms possibly relating to or caused by cystic fibrosis.

Cystic fibrosis related symptoms include, but are not limited to, perturbations in the body's secretion of mucus and sweat, as well as associated complications and symptoms in the respiratory system, digestive system, and reproductive system. For example, a cystic fibrosis patient may routinely exhibit large amounts of thick, sticky, sometimes bloody mucus accumulating in the lung and airways. This buildup of mucus may result in coughing, wheezing or shortness of breath, and can also make it easier for bacteria to cause infections in the respiratory system. An infection caused by unusual pathogens that do not respond to standard antibiotics, such as lung infections caused by mucoid Pseudomonas, may be a sign of cystic fibrosis. Additional cystic fibrosis related symptoms may include sinus infections, bronchitis or pneumonia, growths (i.e., polyps) in the nose.

A cystic fibrosis patient may exhibit mucus obstructed tubes in the pancreas. These blockages prevent the delivery of digestive enzymes to the digestive tract, which results in impaired digestion and absorption. Accordingly, cystic fibrosis related symptoms may also include weight loss or failure to gain weight, ongoing diarrhea or bulky, foul-smelling, greasy stools, intestinal blockages, excess gas, constipation, stomach pain and discomfort. In the long term, these digestive system complications could result in malnutrition, pancreatitis, rectal prolapse, liver diseases, diabetes, and gallstones.

Cystic fibrosis related signs and symptoms may also include infertility, low bone density and related bone-thinning disorders such as osteoporosis, very salty sweat, dehydration, bodily fluid imbalance and ensuing increased heart rate, fatigue, weakness, low blood pressure, heat stroke, and widening and rounding of fingertips and toes known as clubbing.

In some embodiments, the treatment of cystic fibrosis comprises one or more of infection control therapy, chest physical therapy, airway clearance therapy, nutrition therapy, and organ transplantation.

In any of the above embodiments, the anti-cystic fibrosis therapeutic agent is one or more agents selected from the group consisting of penicillin, amoxicillin, cephalosporins, macrolides, fluoroquinolones, sulfonamides, Tetracyclines, aminoglycosides, colistin, Amcinonide, Betamethosone diproprionate, Clobetasol, Clocortolone, Dexamethasone, Diflorasone, Dutasteride, Flumethasone Pivalate, Flunisolide, Fluocinolone Acetonide, Fluocinonide, Fluorometholone, Fluticasone propionate, Fluticasone propionate, Fluticasone propionate, Flurandrenolide, Hydroflumethiazide, aceclofenac, acemetacin, aspirin, celecoxib, dexibuprofen, dexketoprofen, diclofenac, etodolac, etoricoxib, fenoprofen, flurbiprofen, ibuprofen, indometacin, ketoprofen, mefenamic acid, meloxicam, nabumetone, naproxen, sulindac, tenoxicam, tiaprofenic acid, expectorants, antihistamines, cough suppressants, Dextromethorphan, hypertonic salines, dornase alfa, mucolytics, pancreatic enzymes, vitamin A, vitamin D, vitamin E, vitamin K, and supplements reduce stomach acid.

Kits

The present disclosure provides kits for detecting one or more mutations in a sample CFTR nucleic acid in a dried biological fluid sample. In some embodiments, the kits comprise a skin puncture tool, a volumetric absorptive microsampling device, a lysis buffer, and proteinase K, wherein the one or more mutations comprises one or more mutations listed in Table 2. The lysis buffer may comprise guanidine hydrochloride, Tris.Cl, EDTA, Tween 20, and Triton X-100. In other embodiments, the lysis buffer comprises 2.5-10% sodium dodecyl sulphate.

In some embodiments, the kits further comprise one or more components for denaturing nucleoprotein complexes in cells present in the dried biological fluid sample. Additionally or alternatively, in some embodiments, the kits further comprise one or more components for removing protein contaminants, inactivating nuclease activity, and/or removing biological and/or chemical contaminants present in the dried biological fluid sample.

In some embodiments, the kits further comprise one or more primer pairs that hybridize to one or more target segments of the sample CFTR nucleic acid. Additionally or alternatively, in some embodiments, the kits further comprise one or more bait sequences that hybridize to one or more target segments of the sample CFTR nucleic acid. In some embodiments, the target segments of the sample CFTR nucleic acid correspond to a coding or non-coding region of the CFTR gene, such as an exon or intron region. In some embodiments, the target segments of the sample CFTR nucleic acid correspond to a regulatory sequence of the CFTR region, such as a CFTR promoter region or a downstream regulatory region. In some embodiments, the target segments of the sample CFTR nucleic acid may include one or more CFTR mutations listed in Table 2.

Particularly, in some embodiments, kits of the present technology comprise one or more primer pairs or bait sequences that selectively hybridize to, and are useful in amplifying or capturing one or more target segments of the sample CFTR nucleic acid. Particularly, in some embodiments, the target segments of the sample CFTR nucleic acid correspond to a coding or non-coding region of the CFTR gene, such as an exon or intron region. In some embodiments, the target segments of the sample CFTR nucleic acid correspond to a regulatory sequence of the CFTR region, such as a CFTR promoter region or a downstream regulatory region. In some embodiments, the target segments of the sample CFTR nucleic acid may include one or more CFTR mutations listed in Table 2.

In some embodiments, the kits of the present technology comprise a single primer pair or bait sequence that hybridizes to one or more target segments of the sample CFTR nucleic acid. Examples of useful primer pairs may be found in PCT/US2014/027870, which is herein incorporated by reference in its entirety. In other embodiments, the kits of the present technology comprise multiple primer pairs or bait sequences that hybridize to multiple target segments of the sample CFTR nucleic acid. In certain embodiments, the kits of the present technology comprise multiple primer pairs or bait sequences comprising more than one primer pair or more than one bait sequence that hybridizes to one or more target segments of the sample CFTR nucleic acid. In some embodiments, the target segments of the sample CFTR nucleic acid correspond to a coding or non-coding region of the CFTR gene, such as an exon or intron region. In some embodiments, the target segments of the sample CFTR nucleic acid correspond to a regulatory sequence of the CFTR region, such as a CFTR promoter region or a downstream regulatory region. Thus, it is contemplated herein that the kits of the present technology can comprise primer pairs or bait sequences that recognize and specifically hybridize to one or more target segments of a sample CFTR nucleic acid.

In any of the above embodiments of the kits of the present technology, the volumetric absorptive microsampling device is a MITRA® tip.

In some embodiments, the kits may comprise a plurality of volumetric absorptive microsampling devices, each having a hollow holder at the proximal end and an absorbent tip at the distal end. The absorbent tip comprises a hydrophilic, polymeric material configured to absorb 30 microliters or less of blood within about 10 seconds or less. The kit also includes a container having a plurality of compartments. Each compartment is configured to releasably engage a volumetric absorptive microsampling device. The container is configured to prevent the absorbent tips of the microsampling devices from abutting the compartment within which the microsampling device is placed.

Additionally or alternatively, in certain embodiments, the kits may include a plurality of access ports with each port associated with an individual compartment. Each port is located to allow printing onto the holder of a volumetric absorptive microsampling device present within the compartment with which the port is associated. In certain embodiments, the holder of a volumetric absorptive microsampling device has a plurality of ribs extending along a length of the holder with the ribs configured to keep the absorbent tip from contacting walls of the container. The container preferably has two parts configured to form tubular shaped compartments. The container may have a first part with a plurality of elongated mounting protrusions each extending along a portion of a different compartment. The hollow end of the holder of the volumetric absorptive microsampling device fits onto the mounting protrusion to releasably fasten the holder onto the mounting protrusion.

In some embodiments, the kits further comprise buffers, enzymes having polymerase activity, enzymes having polymerase activity and lacking 5'→3' exonuclease activity or both 5'→3' and 3'→5' exonuclease activity, enzyme cofactors such as magnesium or manganese, salts, chain extension nucleotides such as deoxynucleoside triphosphates (dNTPs), modified dNTPs, nuclease-resistant dNTPs or labeled dNTPs, necessary to carry out an assay or reaction, such as amplification and/or detection of one or more hereditary cystic fibrosis mutations described herein, in a dried biological fluid sample.

In one embodiment, the kits of the present technology further comprise a positive control nucleic acid sequence and a negative control nucleic acid sequence to ensure the integrity of the assay during experimental runs. The kit may also comprise instructions for use, software for automated analysis, containers, packages such as packaging intended for commercial sale and the like.

The kit may further comprise one or more of: wash buffers and/or reagents, hybridization buffers and/or reagents, labeling buffers and/or reagents, and detection means. The buffers and/or reagents are usually optimized for the particular amplification/detection technique for which the kit is intended. Protocols for using these buffers and reagents for performing different steps of the procedure may also be included in the kit.

genomic DNA from a dried biological fluid sample (e.g., dried blood) collected using a volumetric absorptive microsampling device.

A total of four human subjects were enrolled in the study. Three MITRA® tips of blood were collected from each of 4 blood donors in order to simultaneously test three extraction methods. A fixed volume of 10 µL of blood was collected on each MITRA® Tip collection device via fingerstick. After drying the blood samples, the absorbent tips of the MITRA® Tip collection devices were then placed in 180 µL Buffer G2 (a lysis buffer containing 800 mM guanidine hydrochloride; 30 mM Tris.Cl, pH 8.0; 30 mM EDTA, pH 8.0; 5% Tween 20; 0.5% Triton X-100) and were vortexed for 15 seconds. The remaining sample processing steps for each of the three extraction methods are summarized below:

| Step | Method 1 | Method 2 | Method 3 |
|---|---|---|---|
| 1 | Incubate MITRA® Tip in Buffer G2 at 90° C. for 15 min | — | Incubate MITRA® Tip in Buffer G2 at 90° C. for 15 min |
| 2 | Vortex for 15 sec | — | Vortex for 15 sec |
| 3 | | Add 10 µL Proteinase K | |
| 4 | | Vortex for 15 sec | |
| 5 | Incubate with Proteinase K at 56° C. for 1 hour | Incubate with Proteinase K at 56° C. for 1 hour | Incubate with Proteinase K at 56° C. Overnight |
| 6 | | Vortex 15 sec | |
| 7 | | Aliquot cell lysate to new tube | |
| 8 | Perform remaining genomic DNA extraction on EZ1® Biorobot using Tissue DNA protocol | | |

The kits of the present technology may include components that are used to prepare nucleic acids from a dried biological fluid sample for the subsequent amplification and/or detection of alterations in a sample CFTR nucleic acid (e.g., CFTR mutations disclosed in Table 2). Such sample preparation components can be used to produce nucleic acid extracts from dried biological fluid samples, such as dried serum, dried plasma, or dried whole blood. The test samples used in the above-described methods will vary based on factors such as the assay format, nature of the detection method, and the specific cells or extracts used as the test sample to be assayed. Methods of extracting nucleic acids from samples are well known in the art and can be readily adapted to obtain a sample that is compatible with the system utilized. Automated sample preparation systems for extracting nucleic acids from a test sample are commercially available, e.g., Roche Molecular Systems' COBAS AmpliPrep System, Qiagen's BioRobot 9600, Qiagen's BioRobot EZ1, QIAsymphony, and Applied Biosystems' PRISM™ 6700 sample preparation system.

Extracted genomic DNA was then quantified using Qubit dsDNA HS Assay Kit, which uses a dsDNA intercalating dye that only fluoresces in the presence of dsDNA. Therefore, quantitation of dsDNA using the Qubit® dsDNA HS Assay Kit is not affected by RNA, proteins, salts, or other contaminants that may affect other quantitation methods. Table 1 demonstrates that the DNA yield obtained from each MITRA® tip varied according to the extraction method. It was determined that extraction method 3 (Incubation of MITRA® Tip with Buffer G2 at 90° C. for 15 min, and with Proteinase K at 56° C. overnight) yielded the highest quantity of DNA.

TABLE 1

Range of DNA yield obtained per MITRA® Tip

| Extraction Method | Total DNA yield (ng) |
|---|---|
| 1 | 111-248 |
| 2 | 163-210 |
| 3 | 222-390 |

These results demonstrate that the methods of the present technology are useful for extracting high yields of genomic DNA from a dried biological fluid sample (e.g., dried blood) collected using a volumetric absorptive microsampling device.

EXAMPLES

Example 1

Extraction of Genomic DNA from Dried Blood Samples Collected Using MITRA® Tips

This Example demonstrates that the methods of the present technology are useful for extracting high yields of Example 2

Comparison of DNA Yield Using One-Tip and Dual-Tip Extractions

DNA extractions were performed on lysates eluted from a single MITRA® tip (one-tip extraction) containing dried blood derived from an individual patient. For dual-tip extractions, lysates eluted from two individual MITRA® tips containing dried blood derived from the same patient were combined together. MITRA® tips were incubated with Buffer G2 at 90° C. for 15 min, and with Proteinase K at 56° C. overnight.

Subsequent nucleic acid extraction was performed using the DNA Investigator kit on the QIAsymphony® automated extraction platform according to the manufacturer's instructions. DNA yields from the one-tip and dual-tip extractions were compared (See FIG. 1).

These results demonstrate that dual-tip extraction on average resulted in a 2-fold increase in DNA yield (FIG. 1). These results demonstrate that the methods of the present technology are useful for extracting high yields of genomic DNA from a dried biological fluid sample (e.g., dried blood) collected using a volumetric absorptive microsampling device.

Example 3

CFvantage® Cystic Fibrosis Expanded Screen Using Dried Blood Samples Extracted from MITRA® Tips Genomic DNA was extracted from dried blood specimens obtained from 7 donors. Each extraction was performed using a dried blood specimen collected using a single MITRA® tip, i.e., one-tip extraction as described in Example 2. Extracted DNA was then tested on the CFvantage® Cystic Fibrosis Expanded Panel, which assesses 38 amplicons corresponding to the CFTR gene. The CFvantage® Cystic Fibrosis Expanded Panel covers 162 CFTR mutations that are associated with cystic fibrosis (Table 2). Next generation sequencing was performed on the MiSeq Sequencer. Quality metrics assessing successful sequencing of a covered region include a minimum of 30 reads per covered hotspot.

Figure 2:
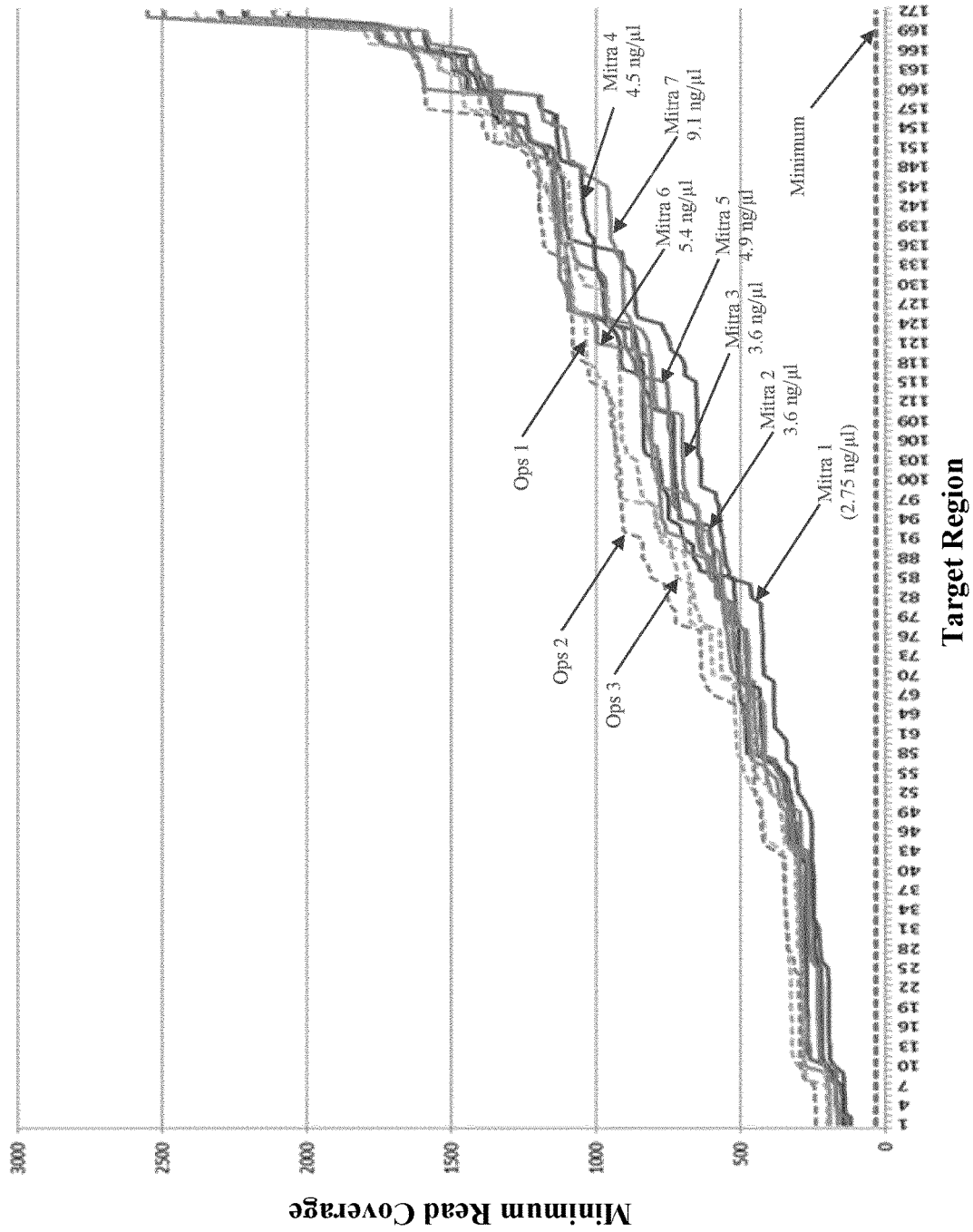
FIG. 2 shows the read coverage per covered CFTR target region (or hotspot) on the Cystic Fibrosis Expanded Panel (CFvantage® Expanded Screen).

Results: As shown in FIG. 2, all 7 samples passed the QC criteria for 100% of the covered hotspot regions.

These results demonstrated that the methods of the present technology are capable of detecting at least one mutation in a sample CFTR nucleic acid in a small-volume dried biological fluid sample that is collected with a volumetric absorptive microsampling device (e.g., MITRA® Tip).

TABLE 2

CF Mutations Detected in the CFvantage ® Cystic Fibrosis Expanded Screen

| Conventional Name | HGVS cDNA Nomenclature |
|---|---|
| 296 + 2T > A | c.164 + 2T > A |
| 394delTT | c.262_263delTT |
| 405 + 1G > A | c.273 + 1G > A |
| 406 − 1G > A | c.274 − 1G > A |
| 444delA | c.313delA |
| 457TAT > G | c.325_327delTATinsG |
| 574delA | c.442delA |
| 621 + 1G > T | c.489 + 1G > T |
| 663delT | c.531delT |
| 711 + 1G > T | c.579 + 1G > T |
| 711 + 3A > G | c.579 + 3A > G |
| 711 + 5G > A | c.579 + 5G > A |
| 712 − 1G > T | c.580 − 1G > T |
| 852del22 | c.720_741del22 |
| 935delA | c.803delA |
| 936delTA | c.805_806delAT |
| 1078delT | c.948delT |
| 1154insTC | c.1022_1023insTC |
| 1161delC | c.1029delC |
| 1213delT | c.1081delT |
| 1248 + 1G > A | c.1116 + 1G > A |
| 1259insA | c.1127_1128insA |
| 1288insTA | c.1153_1154insAT |
| 1341 + 1G > A | c.1209 + 1G > A |
| 1461ins4 | c.1329_1330insAGAT |
| 1525 − 1G > A | c.1393 − 1G > A |
| 1548delG | c.1418delG |
| 1609delCA | c.1477_1478delCA |
| 1677delTA | c.1545_1546delTA |
| 1717 − 1G > A | c.1585 − 1G > A |
| 1717 − 8G > A | c.1585 − 8G > A |
| 1811 + 1.6kbA > G | c.1679 + 1.6kbA > G |
| 1812 − 1G > A | c.1680 − 1G > A |
| 1898 + 1G > A | c.1766 + 1G > A |
| 1898 + 1G > T | c.1766 + 1G > T |
| 1898 + 3A > G | c.1766 + 3A > G |
| 1898 + 5G > T | c.1766 + 5G > T |
| 2043delG | c.1911delG |
| 2055del9 > A | c.1923_1931del9insA |
| 2105del13ins5 | c.1973_1985del13insAGAAA |
| 2108delA | c.1976delA |
| 2143delT | c.2012delT |
| 2183AA > G | c.2051_2052delAAinsG |
| 2184delA | c.2052delA |
| 2184insA | c.2052_2053insA |
| 2307insA | c.2175_2176insA |
| 2347delG | c.2215delG |
| 2585delT | c.2453delT |
| 2622 + 1G > A | c.2490 + 1G > A |
| 2711delT | c.2583delT |
| 2789 + 5G > A | c.2657 + 5G > A |
| 2869insG | c.2737_2738insG |
| 3007delG | c.2875delG |
| 3120 + 1G > A | c.2988 + 1G > A |
| 3120G > A | c.2988G > A |
| 3121 − 1G > A | c.2989 − 1G > A |
| 3171delC | c.3039delC |
| 3199del6 | c.3067_3072delATAGTG |
| 3272 − 26A > G | c.3140 − 26A > G |
| 3659delC | c.3528delC |
| 3667del4 | c.3535_3538delACCA |
| 3791delC | c.3659delC |
| 3821delT | c.3691delT |
| 3849 + 10kbC > T | c.3717 + 12191C > T |
| 3876delA | c.3744delA |
| 3905insT | c.3773_3774insT |
| 4005 + 1G > A | c.3873 + 1G > A |
| 4016insT | c.3884_3885insT |
| 4209TGTT > AA | c.4077_4080delTGTTinsAA |
| 4382delA | c.4251delA |
| A455E | c.1364C > A |
| A559T | c.1675G > A |
| C524X | c.1572C > A |
| CFTRdele2,3 | c.54-5940_273 + 10250del21kb |
| CFTRdele22,23 | c.3964-78_4242 + 577del |
| D110H | c.328G > C |
| D579G | c.1736A > G |
| E60X | c.178G > T |
| E92K | c.274G > A |
| E92X | c.274G > T |
| E585X | c.1753G > T |
| E822X | c.2464G > T |
| E831X | c.2491G > T |
| E1104X | c.3310G > T |
| F311del | c.933_935delCTT |
| F508del | c.1521_1523delCTT |
| G85E[a] | c.254G > A |
| G91R | c.271G > A |
| G178R | c.532G > A |
| G330X | c.988G > T |

TABLE 2-continued

CF Mutations Detected in the CFvantage ®
Cystic Fibrosis Expanded Screen

| Conventional Name | HGVS cDNA Nomenclature |
|---|---|
| G480C | c.1438G > T |
| G542X | c.1624G > T |
| G551D | c.1652G > A |
| G970R | c.2908G > C |
| G1244E | c.3731G > A |
| H199Y | c.595C > T |
| I336K | c.1007T > A |
| I507del | c.1519_1521delATC |
| I1234V | c.3700A > G |
| K710X | c.2128A > T |
| L206W | c.617T > G |
| L467P | c.1400T > C |
| L732X | c.2195T > G |
| L927P | c.2780T > C |
| L1065P | c.3194T > C |
| L1077P | c.3230T > C |
| L1093P | c.3278T > C |
| M1V | c.1A > G |
| M1101K | c.3302T > A |
| N1303K | c.3909C > G |
| P67L | c.200C > T |
| P205S | c.613C > T |
| P574H | c.1721C > A |
| Q39X | c.115C > T |
| Q98X | c.292C > T |
| Q220X | c.658C > T |
| Q493X | c.1477C > T |
| Q525X | c.1573C > T |
| Q552X | c.1654C > T |
| Q890X | c.2668C > T |
| Q1238X | c.3712C > T |
| Q1313X | c.3937C > T |
| R75X | c.223C > T |
| R117C | c.349C > T |
| R117H | c.350G > A |
| R334W | c.1000C > T |
| R347H | c.1040G > A |
| R347P | c.1040G > C |
| R352Q | c.1055G > A |
| R553X | c.1657C > T |
| R560K | c.1679G > A |
| R560T | c.1679G > C |
| R709X | c.2125C > T |
| R764X | c.2290C > T |
| R851X | c.2551C > T |
| R1066C | c.3196C > T |
| R1066H | c.3197G > A |
| R1128X | c.3382A > T |
| R1158X | c.3472C > T |
| R1162X | c.3484C > T |
| R1283M | c.3848G > T |
| S341P | c.1021T > C |
| S466X | c.1397C > A or c.1397C > G |
| S489X | c.1466C > A |
| S492F | c.1475C > T |
| S549N | c.1646G > A |
| S549R | c.1645A > C or c.1647T > G |
| S945L | c.2834C > T |
| S1196X | c.3587C > G |
| S1251N | c.3752G > A |
| S1255X | c.3764C > A |
| T338I | c.1013C > T |
| V520F | c.1558G > T |
| W401X | c.1202G > A or c.1203G > A |
| W846X | c.2537G > A |
| W1089X | c.3266G > A |
| W1145X | c.3435G > A |
| W1204X | c.3611G > A or c.3612G > A |
| W1282X | c.3846G > A |
| Y122X | c.366T > A |
| Y1092X | c.3276C > A or c.3276C > G |
| S364P | c.1090T > C |

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

The terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

What is claimed is:

1. A method for detecting at least one mutation in a pool of nucleic acid samples comprising
   (a) eluting at least two dried biological fluid samples, each having a volume of 20 μL or less and containing about 100 ng to 400 ng of genomic DNA, from at least two absorbent tips of microsampling devices, each of the at least absorbent tips comprising a separate dried biological fluid sample, by contacting the least two absorbent tips of the microsampling devices with a Proteinase K and a lysis buffer comprising guanidine hydrochloride, Tris.Cl, EDTA, and a nonionic surfactant;

(b) extracting from at least two nucleic acid samples of genomic DNA comprising a sample cystic fibrosis transmembrane regulator (CFTR) nucleic acid from the at least two dried biological fluid samples eluted from the at least two absorbent tips of microsampling devices;

(c) generating at least two libraries comprising amplicons corresponding to a plurality of target segments of each of the sample CFTR nucleic acids from each of the at least two nucleic acid samples, wherein each of the at least two libraries of amplicons comprises an index sequence;

(d) pooling the at least two libraries of amplicons; and (e) detecting at least one mutation in at least one of the amplicons in the at least two libraries using high throughput massive parallel sequencing.

2. The method of claim 1, wherein the dried biological fluid sample is dried plasma, dried serum, or dried whole blood.

3. The method of claim 1, wherein the microsampling device is a volumetric absorbent microsampling device.

4. The method of claim 1, wherein the sample volume of the microsampling device is no more than 20 μL.

5. The method of claim 1, wherein the at least one mutation is selected from among a base change, a gene deletion, a gene duplication or a mutation selected from:

| Conventional Name | HGVS cDNA Nomenclature |
|---|---|
| 296 + 2T > A | c.164 + 2T > A |
| 394delTT | c.262_263delTT |
| 405 + 1G > A | c.273 + 1G > A |
| 406 − 1G > A | c.274 − 1G > A |
| 444delA | c.313delA |
| 457TAT > G | c.325_327delTATinsG |
| 574delA | c.442delA |
| 621 + 1G > T | c.489 + 1G > T |
| 663delT | c.531delT |
| 711 + 1G > T | c.579 + 1G > T |
| 711 + 3A > G | c.579 + 3A > G |
| 711 + 5G > A | c.579 + 5G > A |
| 712 − 1G > T | c.580 − 1G > T |
| 852del22 | c.720_741del22 |
| 935delA | c.803delA |
| 936delTA | c.805_806delAT |
| 1078delT | c.948delT |
| 1154insTC | c.1022_1023insTC |
| 1161delC | c.1029delC |
| 1213delT | c.1081delT |
| 1248 + 1G > A | c.1116 + 1G > A |
| 1259insA | c.1127_1128insA |
| 1288insTA | c.1153_1154insAT |
| 1341 + 1G > A | c.1209 + 1G > A |
| 1461ins4 | c.1329_1330insAGAT |
| 1525 − 1G > A | c.1393 − 1G > A |
| 1548delG | c.1418delG |
| 1609delCA | c.1477_1478delCA |
| 1677delTA | c.1545_1546delTA |
| 1717 − 1G > A | c.1585 − 1G > A |
| 1717 − 8G > A | c.1585 − 8G > A |
| 1811 + 1.6kbA > G | c.1679 + 1.6kbA > G |
| 1812 − 1G > A | c.1680 − 1G > A |
| 1898 + 1G > A | c.1766 + 1G > A |
| 1898 + 1G > T | c.1766 + 1G > T |
| 1898 + 3A > G | c.1766 + 3A > G |
| 1898 + 5G > T | c.1766 + 5G > T |
| 2043delG | c.1911delG |
| 2055del9 > A | c.1923_1931del9insA |
| 2105del13ins5 | c.1973_1985del13insAGAAA |

-continued

| Conventional Name | HGVS cDNA Nomenclature |
|---|---|
| 2108delA | c.1976delA |
| E831X | c.2491G > T |
| E1104X | c.3310G > T |
| F311del | c.933_935delCTT |
| F508del | c.1521_1523delCTT |
| G85E$^a$ | c.254G > A |
| G91R | c.271G > A |
| G178R | c.532G > A |
| G330X | c.988G > T |
| G480C | c.1438G > T |
| G542X | c.1624G > T |
| G551D | c.1652G > A |
| G970R | c.2908G > C |
| G1244E | c.3731G > A |
| H199Y | c.595C > T |
| I336K | c.1007T > A |
| I507del | c.1519_1521delATC |
| I1234V | c.3700A > G |
| K710X | c.2128A > T |
| L206W | c.617T > G |
| L467P | c.1400T > C |
| L732X | c.2195T > G |
| L927P | c.2780T > C |
| L1065P | c.3194T > C |
| L1077P | c.3230T > C |
| L1093P | c.3278T > C |
| M1V | c.1A > G |
| M1101K | c.3302T > A |
| N1303K | c.3909C > G |
| P67L | c.200C > T |
| P205S | c.613C > T |
| P574H | c.1721C > A |
| Q39X | c.115C > T |
| Q98X | c.292C > T |
| Q220X | c.658C > T |
| Q493X | c.1477C > T |
| Q525X | c.1573C > T |
| Q552X | c.1654C > T |
| Q890X | c.2668C > T |
| Q1238X | c.3712C > T |
| Q1313X | c.3937C > T |
| 2143delT | c.2012delT |
| 2183AA > G | c.2051_2052delAAinsG |
| 2184delA | c.2052delA |
| 2184insA | c.2052_2053insA |
| 2307insA | c.2175_2176insA |
| 2347delG | c.2215delG |
| 2585delT | c.2453delT |
| 2622 + 1G > A | c.2490 + 1G > A |
| 2711delT | c.2583delT |
| 2789 + 5G > A | c.2657 + 5G > A |
| 2869insG | c.2737_2738insG |
| 3007delG | c.2875delG |
| 3120 + 1G > A | c.2988 + 1G > A |
| 3120G > A | c.2988G > A |
| 3121 − 1G > A | c.2989 − 1G > A |
| 3171delC | c.3039delC |
| 3199del6 | c.3067_3072delATAGTG |
| 3272 − 26A > G | c.3140 − 26A > G |
| 3659delC | c.3528delC |
| 3667del4 | c.3535_3538delACCA |
| 3791delC | c.3659delC |
| 3821delT | c.3691delT |
| 3849 + 10kbC > T | c.3717 + 12191C > T |
| 3876delA | c.3744delA |
| 3905insT | c.3773_3774insT |
| 4005 + 1G > A | c.3873 + 1G > A |
| 4016insT | c.3884_3885insT |
| 4209TGTT > AA | c.4077_4080delTGTTinsAA |
| 4382delA | c.4251delA |
| A455E | c.1364C > A |
| A559T | c.1675G > A |
| C524X | c.1572C > A |
| CFTRdele2,3 | c.54-5940_273 + 10250del21kb |
| CFTRdele22,23 | c.3964-78_4242 + 577del |
| D110H | c.328G > C |

-continued

| Conventional Name | HGVS cDNA Nomenclature |
|---|---|
| D579G | c.1736A > G |
| E60X | c.178G > T |
| E92K | c.274G > A |
| E92X | c.274G > T |
| E585X | c.1753G > T |
| E822X | c.2464G > T |
| R75X | c.223C > T |
| R117C | c.349C > T |
| R117H | c.350G > A |
| R334W | c.1000C > T |
| R347H | c.1040G > A |
| R347P | c.1040G > C |
| R352Q | c.1055G > A |
| R553X | c.1657C > T |
| R560K | c.1679G > A |
| R560T | c.1679G > C |
| R709X | c.2125C > T |
| R764X | c.2290C > T |
| R851X | c.2551C > T |
| R1066C | c.3196C > T |
| R1066H | c.3197G > A |
| R1128X | c.3382A > T |
| R1158X | c.3472C > T |
| R1162X | c.3484C > T |
| R1283M | c.3848G > T |
| S341P | c.1021T > C |
| S466X | c.1397C > A or c.1397C > G |
| S489X | c.1466C > A |
| S492F | c.1475C > T |
| S549N | c.1646G > A |
| S549R | c.1645A > C or c.1647T > G |
| S945L | c.2834C > T |
| S1196X | c.3587C > G |
| S1251N | c.3752G > A |
| S1255X | c.3764C > A |
| T338I | c.1013C > T |
| V520F | c.1558G > T |
| W401X | c.1202G > A or c.1203G > A |
| W846X | c.2537G > A |
| W1089X | c.3266G > A |
| W1145X | c.3435G > A |
| W1204X | c.3611G > A or c.3612G > A |
| W1282X | c.3846G > A |
| Y122X | c.366T > A |
| Y1092X | c.3276C > A or c.3276C > G |
| S364P | c. 1090T > C. |

6. The method of claim 1, wherein the at least one mutation is associated with cystic fibrosis.

7. The method of claim 1, wherein the dried biological fluid sample is obtained from an individual exhibiting cystic fibrosis symptoms, or having a family history of cystic fibrosis or a CFTR mutation or a male partner of an obstetrics and gynecology patient having cystic fibrosis or at least one CFTR mutation.

8. The method of claim 1, wherein the plurality of target segments, together, span all coding and non-coding regions of the CFTR gene, and optionally further span about 1000 nucleotides of a promoter region immediately upstream of the first exon of the CFTR gene or about 200 to 350 nucleotides immediately downstream of the CFTR gene.

9. The method of claim 1, wherein the high throughput massive parallel sequencing involves a read depth approach or is performed using pyrosequencing, reversible dye-terminator sequencing, Ion semiconductor sequencing, single molecule sequencing, sequencing by synthesis, sequencing by ligation, or next generation sequencing.

10. A method for detecting at least one mutation in a pooled sample of cystic fibrosis transmembrane regulator (CFTR) nucleic acids comprising generating a library comprising amplicons corresponding to a plurality of target segments of the pooled sample of CFTR nucleic acids, wherein the pooled sample of CFTR nucleic acids was extracted from dried biological fluid samples obtained from at least two subjects and eluted from an absorbent tip of a microsampling device by contacting the absorbent tip of the microsampling device with a lysis buffer for up to 15 minutes at 90° C. and Proteinase K for up to 18 hours at 56° C., wherein no more than 400 ng of genomic DNA is eluted from the absorbent tip of the microsampling device by contacting the absorbent tip of the microsampling device with (i) a lysis buffer comprising guanidine hydrochloride, Tris.Cl, EDTA, and a nonionic surfactant and (ii) Proteinase K, wherein the at least one mutation in the pooled sample CFTR of nucleic acid is detected using high throughput massive parallel sequencing.

11. The method of claim 1, wherein the plurality of target segments of comprise at least one alteration compared to the corresponding region of a reference CFTR nucleotide sequence, optionally wherein the reference CFTR nucleotide sequence comprises a wild-type CFTR nucleic acid sequence.

12. A method for selecting a patient exhibiting cystic fibrosis symptoms, or a patient at risk for cystic fibrosis for treatment with an anti-cystic fibrosis therapeutic agent comprising
 (a) eluting a dried biological fluid sample of the patient from an absorbent tip of a microsampling device by contacting the absorbent tip of the microsampling device with a lysis buffer comprising guanidine hydrochloride, Tris.Cl, EDTA, and a nonionic surfactant for up to 15 minutes at 90° C. and Proteinase K for up to 18 hours at 56° C., wherein no more than 400 ng of genomic DNA is eluted from the absorbent tip of the microsampling device, wherein the dried biological fluid sample comprises a sample cystic fibrosis transmembrane regulator (CFTR) nucleic acid;
 (b) generating a library comprising amplicons corresponding to a plurality of target segments of the sample CFTR nucleic acid, wherein the of amplicons comprises an index sequence;
 (c) pooling the library of amplicons generated from the patient with at least one other library of amplicons to form a pooled library of amplicons;
 (d) detecting at least one mutation in at least one of the amplicons in the pooled library of amplicons using high throughput massive parallel sequencing; and
 (e) selecting the patient for treatment with an anti-cystic fibrosis therapeutic agent, optionally wherein the anti-cystic fibrosis therapeutic agent is one or more agents selected from the group consisting of penicillin, amoxicillin, cephalosporins, macrolides, fluoroquinolones, sulfonamides, Tetracyclines, aminoglycosides, colistin, Amcinonide, Betamethosone diproprionate, Clobetasol, Clocortolone, Dexamethasone, Diflorasone, Dutasteride, Flumethasone Pivalate, Flunisolide, Fluocinolone Acetonide, Fluocinonide, Fluorometholone, Fluticasone propionate, Fluticasone propionate, Fluticasone propionate, Flurandrenolide, Hydroflumethiazide, aceclofenac, acemetacin, aspirin, celecoxib, dexibuprofen, dexketoprofen, diclofenac, etodolac, etoricoxib, fenoprofen, flurbiprofen, ibuprofen, indometacin, ketoprofen, mefenamic acid, meloxicam, nabumetone, naproxen, sulindac, tenoxicam, tiaprofenic acid, expectorants, antihistamines, cough suppressants, Dextromethorphan, hypertonic salines, dornase alfa, mucolytics, pancreatic enzymes, vitamin A, vitamin D, vitamin E, vitamin K, and supplements reduce stomach acid.

13. The method of claim 1, wherein the dried biological fluid sample was collected from a patient via fingerstick.

14. The method of claim 1, wherein about 100 ng to about 400 ng of genomic DNA is eluted from the absorbent tip of the microsampling device.

15. The method of claim 1, wherein eluting comprises contacting the absorbent tip of the microsampling device with the lysis buffer for up to 15 minutes at 90° C. and Proteinase K for up to 18 hours at 56° C.

* * * * *